United States Patent
Lee et al.

(10) Patent No.: US 11,935,637 B2
(45) Date of Patent: Mar. 19, 2024

(54) ONBOARDING AND TOTAL DAILY INSULIN ADAPTIVITY

(71) Applicant: INSULET CORPORATION, Acton, MA (US)

(72) Inventors: Joon Bok Lee, Acton, MA (US); Yibin Zheng, Hartland, WI (US); Jason O'Connor, Acton, MA (US); Trang Ly, Concord, MA (US); Eric Benjamin, Acton, MA (US)

(73) Assignee: INSULET CORPORATION, Acton, MA (US)

(*) Notice: Subject to any disclaimer, the term of this patent is extended or adjusted under 35 U.S.C. 154(b) by 665 days.

(21) Appl. No.: 16/586,499

(22) Filed: Sep. 27, 2019

(65) Prior Publication Data
US 2021/0098105 A1    Apr. 1, 2021

(51) Int. Cl.
*G16H 20/17* (2018.01)
*A61M 5/172* (2006.01)
*G16H 40/67* (2018.01)

(52) U.S. Cl.
CPC .......... *G16H 20/17* (2018.01); *A61M 5/1723* (2013.01); *G16H 40/67* (2018.01);
(Continued)

(58) Field of Classification Search
CPC ........ G16H 40/67; G16H 50/50; G16H 40/40; A61M 5/1723; A61M 2205/3584; A61M 2205/505; A61M 2230/201
(Continued)

(56) References Cited

U.S. PATENT DOCUMENTS 303,013 A   8/1884 Horton
2,797,149 A  6/1957 Skeggs
(Continued)

FOREIGN PATENT DOCUMENTS

AU   2015200834 A1   3/2015
AU   2015301146 A1   3/2017
(Continued)

OTHER PUBLICATIONS

US 5,954,699 A, 09/1999, Jost et al. (withdrawn)
(Continued)

*Primary Examiner* — Dilek B Cobanoglu
(74) *Attorney, Agent, or Firm* — GOODWIN PROCTER LLP

(57) ABSTRACT

Disclosed are a device, a computer-readable medium, and techniques that provide an onboarding process and an adaptivity process for a drug delivery device. A processor executing an onboarding process determines whether a history of delivered insulin to a user meets certain sufficiency requirements. The onboarding process enables a processor to cause the drug delivery device to administer doses of insulin to a user according to an initial total daily insulin dose calculation that is determined based on the sufficiency of the insulin delivery history. The initial total daily insulin may be adapted according to the adaptivity process as new insulin delivery is collected. The insulin delivery history, when sufficient, may be used to set total daily insulin dosages that enable automated insulin delivery upon replacement of a drug delivery device. The adaptivity process may be implemented to modify an initial insulin delivery doses to provide adapted insulin delivery doses.

14 Claims, 7 Drawing Sheets

(52) U.S. Cl.
CPC . *A61M 2205/18* (2013.01); *A61M 2205/3584* (2013.01); *A61M 2205/505* (2013.01); *A61M 2230/201* (2013.01)

(58) Field of Classification Search
USPC ........................................................ 700/282
See application file for complete search history.

(56) References Cited

U.S. PATENT DOCUMENTS

| | | | |
|---|---|---|---|
| 3,631,847 A | 1/1972 | Hobbs | |
| 3,634,039 A | 1/1972 | Brondy | |
| 3,812,843 A | 5/1974 | Wootten et al. | |
| 3,841,328 A | 10/1974 | Jensen | |
| 3,963,380 A | 6/1976 | Thomas, Jr. et al. | |
| 4,055,175 A | 10/1977 | Clemens et al. | |
| 4,146,029 A | 3/1979 | Ellinwood, Jr. | |
| 4,151,845 A | 5/1979 | Clemens | |
| 4,245,634 A | 1/1981 | Albisser et al. | |
| 4,368,980 A | 1/1983 | Aldred et al. | |
| 4,373,527 A | 2/1983 | Fischell | |
| 4,403,984 A | 9/1983 | Ash et al. | |
| 4,464,170 A | 8/1984 | Clemens et al. | |
| 4,469,481 A | 9/1984 | Kobayashi | |
| 4,475,901 A | 10/1984 | Kraegen et al. | |
| 4,526,568 A | 7/1985 | Clemens et al. | |
| 4,526,569 A | 7/1985 | Bernardi | |
| 4,529,401 A | 7/1985 | Leslie et al. | |
| 4,559,033 A | 12/1985 | Stephen et al. | |
| 4,559,037 A | 12/1985 | Franetzki et al. | |
| 4,573,968 A | 3/1986 | Parker | |
| 4,624,661 A | 11/1986 | Arimond | |
| 4,633,878 A | 1/1987 | Bombardieri | |
| 4,657,529 A | 4/1987 | Prince et al. | |
| 4,685,903 A | 8/1987 | Cable et al. | |
| 4,731,726 A | 3/1988 | Allen, III | |
| 4,743,243 A | 5/1988 | Vaillancourt | |
| 4,755,173 A | 7/1988 | Konopka et al. | |
| 4,781,688 A | 11/1988 | Thoma et al. | |
| 4,781,693 A | 11/1988 | Martinez et al. | |
| 4,808,161 A | 2/1989 | Kamen | |
| 4,854,170 A | 8/1989 | Brimhall et al. | |
| 4,886,499 A | 12/1989 | Cirelli et al. | |
| 4,900,292 A | 2/1990 | Berry et al. | |
| 4,919,596 A | 4/1990 | Slate et al. | |
| 4,925,444 A | 5/1990 | Orkin et al. | |
| 4,940,527 A | 7/1990 | Kazlauskas et al. | |
| 4,975,581 A | 12/1990 | Robinson et al. | |
| 4,976,720 A | 12/1990 | Machold et al. | |
| 4,981,140 A | 1/1991 | Wyatt | |
| 4,994,047 A | 2/1991 | Walker et al. | |
| 5,007,286 A | 4/1991 | Malcolm et al. | |
| 5,097,834 A | 3/1992 | Skrabal | |
| 5,102,406 A | 4/1992 | Arnold | |
| 5,109,850 A | 5/1992 | Blanco et al. | |
| 5,125,415 A | 6/1992 | Bell | |
| 5,134,079 A | 7/1992 | Cusack et al. | |
| 5,153,827 A | 10/1992 | Coutre et al. | |
| 5,165,406 A | 11/1992 | Wong | |
| 5,176,662 A | 1/1993 | Bartholomew et al. | |
| 5,178,609 A | 1/1993 | Ishikawa | |
| 5,207,642 A | 5/1993 | Orkin et al. | |
| 5,232,439 A | 8/1993 | Campbell et al. | |
| 5,237,993 A | 8/1993 | Skrabal | |
| 5,244,463 A | 9/1993 | Cordner, Jr. et al. | |
| 5,257,980 A | 11/1993 | Van Antwerp et al. | |
| 5,273,517 A | 12/1993 | Barone et al. | |
| 5,281,808 A | 1/1994 | Kunkel | |
| 5,299,571 A | 4/1994 | Mastrototaro | |
| 5,308,982 A | 5/1994 | Ivaldi et al. | |
| 5,342,298 A | 8/1994 | Michaels et al. | |
| 5,377,674 A | 1/1995 | Kuestner | |
| 5,380,665 A | 1/1995 | Cusack et al. | |
| 5,385,539 A | 1/1995 | Maynard | |
| 5,389,078 A | 2/1995 | Zalesky | |
| 5,411,889 A | 5/1995 | Hoots et al. | |
| 5,468,727 A | 11/1995 | Phillips et al. | |
| 5,505,709 A | 4/1996 | Funderburk et al. | |
| 5,505,828 A | 4/1996 | Wong et al. | |
| 5,507,288 A | 4/1996 | Bocker et al. | |
| 5,533,389 A | 7/1996 | Kamen et al. | |
| 5,558,640 A | 9/1996 | Pfeiler et al. | |
| 5,569,186 A | 10/1996 | Lord et al. | |
| 5,584,813 A | 12/1996 | Livingston et al. | |
| 5,609,572 A | 3/1997 | Lang | |
| 5,665,065 A | 9/1997 | Colman et al. | |
| 5,678,539 A | 10/1997 | Schubert et al. | |
| 5,685,844 A | 11/1997 | Marttila | |
| 5,685,859 A | 11/1997 | Komerup | |
| 5,693,018 A | 12/1997 | Kriesel et al. | |
| 5,697,899 A | 12/1997 | Hillman et al. | |
| 5,700,695 A | 12/1997 | Yassinzadeh et al. | |
| 5,703,364 A | 12/1997 | Rosenthal | |
| 5,714,123 A | 2/1998 | Sohrab | |
| 5,716,343 A | 2/1998 | Kriesel et al. | |
| 5,722,397 A | 3/1998 | Eppstein | |
| 5,741,228 A | 4/1998 | Lambrecht et al. | |
| 5,746,217 A | 5/1998 | Erickson et al. | |
| 5,755,682 A | 5/1998 | Knudson et al. | |
| 5,758,643 A | 6/1998 | Wong et al. | |
| 5,800,405 A | 9/1998 | McPhee | |
| 5,800,420 A | 9/1998 | Gross et al. | |
| 5,801,057 A | 9/1998 | Smart et al. | |
| 5,804,048 A | 9/1998 | Wong et al. | |
| 5,817,007 A | 10/1998 | Fodgaard et al. | |
| 5,820,622 A | 10/1998 | Gross et al. | |
| 5,823,951 A | 10/1998 | Messerschmidt | |
| 5,840,020 A | 11/1998 | Heinonen et al. | |
| 5,848,991 A | 12/1998 | Gross et al. | |
| 5,851,197 A | 12/1998 | Marano et al. | |
| 5,858,005 A | 1/1999 | Kriesel | |
| 5,865,806 A | 2/1999 | Howell | |
| 5,871,470 A | 2/1999 | McWha | |
| 5,879,310 A | 3/1999 | Sopp et al. | |
| 5,902,253 A | 5/1999 | Pfeiffer et al. | |
| 5,931,814 A | 8/1999 | Alex et al. | |
| 5,932,175 A | 8/1999 | Knute et al. | |
| 5,935,099 A | 8/1999 | Peterson et al. | |
| 5,947,911 A | 9/1999 | Wong et al. | |
| 5,971,941 A | 10/1999 | Simons et al. | |
| 5,993,423 A | 11/1999 | Choi | |
| 5,997,501 A | 12/1999 | Gross et al. | |
| 6,017,318 A | 1/2000 | Gauthier et al. | |
| 6,024,539 A | 2/2000 | Blomquist | |
| 6,032,059 A | 2/2000 | Henning et al. | |
| 6,036,924 A | 3/2000 | Simons et al. | |
| 6,040,578 A | 3/2000 | Malin et al. | |
| 6,049,727 A | 4/2000 | Crothall | |
| 6,050,978 A | 4/2000 | Orr et al. | |
| 6,058,934 A | 5/2000 | Sullivan | |
| 6,066,103 A | 5/2000 | Duchon et al. | |
| 6,071,292 A | 6/2000 | Makower et al. | |
| 6,072,180 A | 6/2000 | Kramer et al. | |
| 6,077,055 A | 6/2000 | Vilks | |
| 6,090,092 A | 7/2000 | Fowles et al. | |
| 6,101,406 A | 8/2000 | Hacker et al. | |
| 6,102,872 A | 8/2000 | Doneen et al. | |
| 6,115,673 A | 9/2000 | Malin et al. | |
| 6,123,827 A | 9/2000 | Wong et al. | |
| 6,124,134 A | 9/2000 | Stark | |
| 6,126,637 A | 10/2000 | Kriesel et al. | |
| 6,128,519 A | 10/2000 | Say | |
| 6,142,939 A | 11/2000 | Eppstein et al. | |
| 6,143,164 A | 11/2000 | Heller et al. | |
| 6,157,041 A | 12/2000 | Thomas et al. | |
| 6,161,028 A | 12/2000 | Braig et al. | |
| 6,162,639 A | 12/2000 | Douglas | |
| 6,196,046 B1 | 3/2001 | Braig et al. | |
| 6,200,287 B1 | 3/2001 | Keller et al. | |
| 6,200,338 B1 | 3/2001 | Solomon et al. | |
| 6,214,629 B1 | 4/2001 | Freitag et al. | |
| 6,226,082 B1 | 5/2001 | Roe | |
| 6,244,776 B1 | 6/2001 | Wiley | |
| 6,261,065 B1 | 7/2001 | Nayak et al. | |
| 6,262,798 B1 | 7/2001 | Shepherd et al. | |

(56) References Cited

U.S. PATENT DOCUMENTS

| | | | |
|---|---|---|---|
| 6,270,455 | B1 | 8/2001 | Brown |
| 6,271,045 | B1 | 8/2001 | Douglas et al. |
| 6,280,381 | B1 | 8/2001 | Malin et al. |
| 6,285,448 | B1 | 9/2001 | Kunstner |
| 6,309,370 | B1 | 10/2001 | Haim et al. |
| 6,312,888 | B1 | 11/2001 | Wong et al. |
| 6,334,851 | B1 | 1/2002 | Hayes et al. |
| 6,375,627 | B1 | 4/2002 | Mauze et al. |
| 6,379,301 | B1 | 4/2002 | Worthington et al. |
| 6,402,689 | B1 | 6/2002 | Scarantino et al. |
| 6,421,812 | B1 | 7/2002 | Wang et al. |
| 6,470,279 | B1 | 10/2002 | Samsoondar |
| 6,475,196 | B1 | 11/2002 | Vachon |
| 6,477,901 | B1 | 11/2002 | Tadigadapa et al. |
| 6,484,044 | B1 | 11/2002 | Lilienfeld-Toal |
| 6,491,656 | B1 | 12/2002 | Morris |
| 6,512,937 | B2 | 1/2003 | Blank et al. |
| 6,525,509 | B1 | 2/2003 | Petersson et al. |
| 6,528,809 | B1 | 3/2003 | Thomas et al. |
| 6,540,672 | B1 | 4/2003 | Simonsen et al. |
| 6,544,212 | B2 | 4/2003 | Galley et al. |
| 6,546,268 | B1 | 4/2003 | Ishikawa et al. |
| 6,546,269 | B1 | 4/2003 | Kurnik |
| 6,553,841 | B1 | 4/2003 | Blouch |
| 6,554,798 | B1 | 4/2003 | Mann et al. |
| 6,556,850 | B1 | 4/2003 | Braig et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,562,014 | B2 | 5/2003 | Lin et al. |
| 6,569,125 | B2 | 5/2003 | Jepson et al. |
| 6,572,542 | B1 | 6/2003 | Houben et al. |
| 6,572,545 | B2 | 6/2003 | Knobbe et al. |
| 6,574,490 | B2 | 6/2003 | Abbink et al. |
| 6,575,905 | B2 | 6/2003 | Knobbe et al. |
| 6,580,934 | B1 | 6/2003 | Braig et al. |
| 6,618,603 | B2 | 9/2003 | Varalli et al. |
| 6,633,772 | B2 | 10/2003 | Ford et al. |
| 6,645,142 | B2 | 11/2003 | Braig et al. |
| 6,653,091 | B1 | 11/2003 | Dunn et al. |
| 6,662,030 | B2 | 12/2003 | Khalil et al. |
| 6,669,663 | B1 | 12/2003 | Thompson |
| 6,678,542 | B2 | 1/2004 | Braig et al. |
| 6,699,221 | B2 | 3/2004 | Vaillancourt |
| 6,718,189 | B2 | 4/2004 | Rohrscheib et al. |
| 6,721,582 | B2 | 4/2004 | Trepagnier et al. |
| 6,728,560 | B2 | 4/2004 | Kollias et al. |
| 6,740,059 | B2 | 5/2004 | Flaherty |
| 6,740,072 | B2 | 5/2004 | Starkweather et al. |
| 6,751,490 | B2 | 6/2004 | Esenaliev et al. |
| 6,758,835 | B2 | 7/2004 | Close et al. |
| 6,780,156 | B2 | 8/2004 | Haueter et al. |
| 6,810,290 | B2 | 10/2004 | Lebel et al. |
| 6,837,858 | B2 | 1/2005 | Cunningham et al. |
| 6,837,988 | B2 | 1/2005 | Leong et al. |
| 6,846,288 | B2 | 1/2005 | Nagar et al. |
| 6,862,534 | B2 | 3/2005 | Sterling et al. |
| 6,865,408 | B1 | 3/2005 | Abbink et al. |
| 6,890,291 | B2 | 5/2005 | Robinson et al. |
| 6,936,029 | B2 | 8/2005 | Mann et al. |
| 6,949,081 | B1 | 9/2005 | Chance |
| 6,958,809 | B2 | 10/2005 | Sterling et al. |
| 6,989,891 | B2 | 1/2006 | Braig et al. |
| 6,990,366 | B2 | 1/2006 | Say et al. |
| 7,008,404 | B2 | 3/2006 | Nakajima |
| 7,009,180 | B2 | 3/2006 | Sterling et al. |
| 7,016,713 | B2 | 3/2006 | Gardner et al. |
| 7,018,360 | B2 | 3/2006 | Flaherty et al. |
| 7,025,743 | B2 | 4/2006 | Mann et al. |
| 7,025,744 | B2 | 4/2006 | Utterberg et al. |
| 7,027,848 | B2 | 4/2006 | Robinson et al. |
| 7,043,288 | B2 | 5/2006 | Davis, III et al. |
| 7,060,059 | B2 | 6/2006 | Keith et al. |
| 7,061,593 | B2 | 6/2006 | Braig et al. |
| 7,096,124 | B2 | 8/2006 | Sterling et al. |
| 7,115,205 | B2 | 10/2006 | Robinson et al. |
| 7,128,727 | B2 | 10/2006 | Flaherty et al. |
| 7,139,593 | B2 | 11/2006 | Kavak et al. |
| 7,139,598 | B2 | 11/2006 | Hull et al. |
| 7,144,384 | B2 | 12/2006 | Gorman et al. |
| 7,171,252 | B1 | 1/2007 | Scarantino et al. |
| 7,190,988 | B2 | 3/2007 | Say et al. |
| 7,204,823 | B2 | 4/2007 | Estes et al. |
| 7,248,912 | B2 | 7/2007 | Gough et al. |
| 7,267,665 | B2 | 9/2007 | Steil et al. |
| 7,271,912 | B2 | 9/2007 | Sterling et al. |
| 7,278,983 | B2 | 10/2007 | Ireland et al. |
| 7,291,107 | B2 | 11/2007 | Hellwig et al. |
| 7,291,497 | B2 | 11/2007 | Holmes et al. |
| 7,303,549 | B2 | 12/2007 | Flaherty et al. |
| 7,303,622 | B2 | 12/2007 | Loch et al. |
| 7,303,922 | B2 | 12/2007 | Jeng et al. |
| 7,354,420 | B2 | 4/2008 | Steil et al. |
| 7,388,202 | B2 | 6/2008 | Sterling et al. |
| 7,402,153 | B2 | 7/2008 | Steil et al. |
| 7,404,796 | B2 * | 7/2008 | Ginsberg .................. A61P 3/10 |
| | | | 600/300 |
| 7,429,255 | B2 | 9/2008 | Thompson |
| 7,460,130 | B2 | 12/2008 | Salganicoff |
| 7,481,787 | B2 | 1/2009 | Gable et al. |
| 7,491,187 | B2 * | 2/2009 | Van Den Berghe ........................ |
| | | | A61M 5/1723 |
| | | | 700/28 |
| 7,500,949 | B2 | 3/2009 | Gottlieb et al. |
| 7,509,156 | B2 * | 3/2009 | Flanders ................ G16H 10/40 |
| | | | 600/347 |
| 7,547,281 | B2 | 6/2009 | Hayes et al. |
| 7,569,030 | B2 | 8/2009 | Lebel et al. |
| 7,608,042 | B2 | 10/2009 | Goldberger et al. |
| 7,651,845 | B2 | 1/2010 | Doyle, III et al. |
| 7,680,529 | B2 | 3/2010 | Kroll |
| 7,734,323 | B2 | 6/2010 | Blomquist et al. |
| 7,766,829 | B2 | 8/2010 | Sloan et al. |
| 7,785,258 | B2 | 8/2010 | Braig et al. |
| 7,806,854 | B2 | 10/2010 | Damiano et al. |
| 7,806,886 | B2 | 10/2010 | Kanderian, Jr. et al. |
| 7,918,825 | B2 | 4/2011 | OConnor et al. |
| 7,946,985 | B2 | 5/2011 | Mastrototaro et al. |
| 7,972,296 | B2 | 7/2011 | Braig et al. |
| 8,221,345 | B2 | 7/2012 | Blomquist |
| 8,251,907 | B2 | 8/2012 | Sterling et al. |
| 8,449,524 | B2 | 5/2013 | Braig et al. |
| 8,452,359 | B2 | 5/2013 | Rebec et al. |
| 8,454,576 | B2 | 6/2013 | Mastrototaro et al. |
| 8,467,980 | B2 | 6/2013 | Campbell et al. |
| 8,478,557 | B2 | 7/2013 | Hayter et al. |
| 8,504,179 | B2 * | 8/2013 | Blomquist ............. G16H 40/40 |
| | | | 700/282 |
| 8,547,239 | B2 | 10/2013 | Peatfield et al. |
| 8,597,274 | B2 | 12/2013 | Sloan et al. |
| 8,622,988 | B2 | 1/2014 | Hayter |
| 8,657,807 | B2 * | 2/2014 | Blomquist .......... G06F 3/04842 |
| | | | 604/890.1 |
| 8,810,394 | B2 | 8/2014 | Kalpin |
| 8,818,782 | B2 * | 8/2014 | Thukral ................. G16H 50/20 |
| | | | 703/11 |
| 9,061,097 | B2 | 6/2015 | Holt et al. |
| 9,171,343 | B1 | 10/2015 | Fischell et al. |
| 9,233,204 | B2 | 1/2016 | Booth et al. |
| 9,486,571 | B2 | 11/2016 | Rosinko |
| 9,579,456 | B2 | 2/2017 | Budiman et al. |
| 9,743,224 | B2 | 8/2017 | San Vicente et al. |
| 9,907,515 | B2 | 3/2018 | Doyle, III et al. |
| 9,980,140 | B1 | 5/2018 | Spencer et al. |
| 9,984,773 | B2 | 5/2018 | Gondhalekar et al. |
| 10,248,839 | B2 | 4/2019 | Levy et al. |
| 10,335,464 | B1 | 7/2019 | Michelich et al. |
| 10,583,250 | B2 | 3/2020 | Mazlish et al. |
| 10,737,024 | B2 | 8/2020 | Schmid |
| 10,987,468 | B2 * | 4/2021 | Mazlish ................. G16H 20/17 |
| 11,197,964 | B2 | 12/2021 | Sjolund et al. |
| 11,260,169 | B2 | 3/2022 | Estes |

(56) References Cited

U.S. PATENT DOCUMENTS

| | | | |
|---|---|---|---|
| 11,628,251 B2 * | 4/2023 | O'Connor | A61M 5/14248 604/65 |
| 2001/0021803 A1 | 9/2001 | Blank et al. | |
| 2001/0034023 A1 | 10/2001 | Stanton, Jr. et al. | |
| 2001/0034502 A1 | 10/2001 | Moberg et al. | |
| 2001/0051377 A1 | 12/2001 | Hammer et al. | |
| 2001/0053895 A1 | 12/2001 | Vaillancourt | |
| 2002/0010401 A1 | 1/2002 | Bushmakin et al. | |
| 2002/0010423 A1 | 1/2002 | Gross et al. | |
| 2002/0016568 A1 | 2/2002 | Lebel et al. | |
| 2002/0040208 A1 | 4/2002 | Flaherty et al. | |
| 2002/0123740 A1 | 9/2002 | Flaherty et al. | |
| 2002/0128543 A1 | 9/2002 | Leonhardt | |
| 2002/0147423 A1 | 10/2002 | Burbank et al. | |
| 2002/0155425 A1 | 10/2002 | Han et al. | |
| 2002/0161288 A1 | 10/2002 | Shin et al. | |
| 2003/0023148 A1 | 1/2003 | Lorenz et al. | |
| 2003/0050621 A1 | 3/2003 | Lebel et al. | |
| 2003/0060692 A1 | 3/2003 | Ruchti et al. | |
| 2003/0086074 A1 | 5/2003 | Braig et al. | |
| 2003/0086075 A1 | 5/2003 | Braig et al. | |
| 2003/0090649 A1 | 5/2003 | Sterling et al. | |
| 2003/0100040 A1 | 5/2003 | Bonnecaze et al. | |
| 2003/0130616 A1 | 7/2003 | Steil et al. | |
| 2003/0135388 A1 | 7/2003 | Martucci et al. | |
| 2003/0144582 A1 | 7/2003 | Cohen et al. | |
| 2003/0163097 A1 | 8/2003 | Fleury et al. | |
| 2003/0195404 A1 | 10/2003 | Knobbe et al. | |
| 2003/0208113 A1 | 11/2003 | Mault et al. | |
| 2003/0208154 A1 | 11/2003 | Close et al. | |
| 2003/0212379 A1 | 11/2003 | Bylund et al. | |
| 2003/0216627 A1 | 11/2003 | Lorenz et al. | |
| 2003/0220605 A1 | 11/2003 | Bowman, Jr. et al. | |
| 2004/0010207 A1 | 1/2004 | Flaherty et al. | |
| 2004/0034295 A1 | 2/2004 | Salganicoff | |
| 2004/0045879 A1 | 3/2004 | Shults et al. | |
| 2004/0051368 A1 | 3/2004 | Caputo et al. | |
| 2004/0064259 A1 | 4/2004 | Haaland et al. | |
| 2004/0097796 A1 | 5/2004 | Berman et al. | |
| 2004/0116847 A1 | 6/2004 | Wall | |
| 2004/0122353 A1 | 6/2004 | Shahmirian et al. | |
| 2004/0133166 A1 | 7/2004 | Moberg et al. | |
| 2004/0147034 A1 | 7/2004 | Gore et al. | |
| 2004/0171983 A1 | 9/2004 | Sparks et al. | |
| 2004/0203357 A1 | 10/2004 | Nassimi | |
| 2004/0204868 A1 | 10/2004 | Maynard et al. | |
| 2004/0215492 A1 | 10/2004 | Choi | |
| 2004/0220517 A1 | 11/2004 | Starkweather et al. | |
| 2004/0241736 A1 | 12/2004 | Hendee et al. | |
| 2004/0249308 A1 | 12/2004 | Forssell | |
| 2005/0003470 A1 | 1/2005 | Nelson et al. | |
| 2005/0020980 A1 | 1/2005 | Inoue et al. | |
| 2005/0022274 A1 | 1/2005 | Campbell et al. | |
| 2005/0033148 A1 | 2/2005 | Haueter et al. | |
| 2005/0049179 A1 | 3/2005 | Davidson et al. | |
| 2005/0065464 A1 | 3/2005 | Talbot et al. | |
| 2005/0065465 A1 | 3/2005 | Lebel et al. | |
| 2005/0075624 A1 | 4/2005 | Miesel | |
| 2005/0105095 A1 | 5/2005 | Pesach et al. | |
| 2005/0137573 A1 | 6/2005 | McLaughlin | |
| 2005/0171503 A1 | 8/2005 | Van Den Berghe et al. | |
| 2005/0182306 A1 | 8/2005 | Sloan | |
| 2005/0192494 A1 | 9/2005 | Ginsberg | |
| 2005/0192557 A1 | 9/2005 | Brauker et al. | |
| 2005/0197621 A1 | 9/2005 | Poulsen et al. | |
| 2005/0203360 A1 | 9/2005 | Brauker et al. | |
| 2005/0203461 A1 | 9/2005 | Flaherty et al. | |
| 2005/0238507 A1 | 10/2005 | Dilanni et al. | |
| 2005/0261660 A1 | 11/2005 | Choi | |
| 2005/0272640 A1 | 12/2005 | Doyle, III et al. | |
| 2005/0277912 A1 | 12/2005 | John | |
| 2006/0009727 A1 | 1/2006 | OMahony et al. | |
| 2006/0079809 A1 | 4/2006 | Goldberger et al. | |
| 2006/0100494 A1 | 5/2006 | Kroll | |
| 2006/0134323 A1 | 6/2006 | OBrien | |
| 2006/0167350 A1 | 7/2006 | Monfre et al. | |
| 2006/0173406 A1 | 8/2006 | Hayes et al. | |
| 2006/0189925 A1 | 8/2006 | Gable et al. | |
| 2006/0189926 A1 | 8/2006 | Hall et al. | |
| 2006/0197015 A1 | 9/2006 | Sterling et al. | |
| 2006/0200070 A1 | 9/2006 | Callicoat et al. | |
| 2006/0204535 A1 | 9/2006 | Johnson | |
| 2006/0229531 A1 | 10/2006 | Goldberger et al. | |
| 2006/0253085 A1 | 11/2006 | Geismar et al. | |
| 2006/0264895 A1 | 11/2006 | Flanders | |
| 2006/0270983 A1 | 11/2006 | Lord et al. | |
| 2006/0276771 A1 | 12/2006 | Galley et al. | |
| 2006/0282290 A1 | 12/2006 | Flaherty et al. | |
| 2007/0016127 A1 | 1/2007 | Staib et al. | |
| 2007/0060796 A1 | 3/2007 | Kim | |
| 2007/0060869 A1 | 3/2007 | Tolle et al. | |
| 2007/0060872 A1 | 3/2007 | Hall et al. | |
| 2007/0083160 A1 | 4/2007 | Hall et al. | |
| 2007/0106135 A1 | 5/2007 | Sloan et al. | |
| 2007/0116601 A1 | 5/2007 | Patton | |
| 2007/0118405 A1 | 5/2007 | Campbell et al. | |
| 2007/0129690 A1 | 6/2007 | Rosenblatt et al. | |
| 2007/0142720 A1 | 6/2007 | Ridder et al. | |
| 2007/0173761 A1 | 7/2007 | Kanderian et al. | |
| 2007/0173974 A1 | 7/2007 | Lin | |
| 2007/0179352 A1 | 8/2007 | Randlov et al. | |
| 2007/0191716 A1 | 8/2007 | Goldberger et al. | |
| 2007/0197163 A1 | 8/2007 | Robertson | |
| 2007/0225675 A1 | 9/2007 | Robinson et al. | |
| 2007/0244381 A1 | 10/2007 | Robinson et al. | |
| 2007/0249007 A1 | 10/2007 | Rosero | |
| 2007/0264707 A1 | 11/2007 | Liederman et al. | |
| 2007/0282269 A1 | 12/2007 | Carter et al. | |
| 2007/0287985 A1 | 12/2007 | Estes et al. | |
| 2007/0293843 A1 | 12/2007 | Ireland et al. | |
| 2008/0033272 A1 | 2/2008 | Gough et al. | |
| 2008/0051764 A1 | 2/2008 | Dent et al. | |
| 2008/0058625 A1 | 3/2008 | McGarraugh et al. | |
| 2008/0065050 A1 | 3/2008 | Sparks et al. | |
| 2008/0071157 A1 | 3/2008 | McGarraugh et al. | |
| 2008/0071158 A1 | 3/2008 | McGarraugh et al. | |
| 2008/0078400 A1 | 4/2008 | Martens et al. | |
| 2008/0097289 A1 | 4/2008 | Steil et al. | |
| 2008/0132880 A1 | 6/2008 | Buchman | |
| 2008/0161664 A1 | 7/2008 | Mastrototaro et al. | |
| 2008/0172026 A1 | 7/2008 | Blomquist | |
| 2008/0177165 A1 | 7/2008 | Blomquist et al. | |
| 2008/0188796 A1 | 8/2008 | Steil et al. | |
| 2008/0200838 A1 | 8/2008 | Goldberger et al. | |
| 2008/0206067 A1 | 8/2008 | De Corral et al. | |
| 2008/0208113 A1 | 8/2008 | Damiano et al. | |
| 2008/0214919 A1 | 9/2008 | Harmon et al. | |
| 2008/0228056 A1 | 9/2008 | Blomquist et al. | |
| 2008/0249386 A1 | 10/2008 | Besterman et al. | |
| 2008/0269585 A1 | 10/2008 | Ginsberg | |
| 2008/0269714 A1 | 10/2008 | Mastrototaro et al. | |
| 2008/0269723 A1 | 10/2008 | Mastrototaro et al. | |
| 2008/0287906 A1 | 11/2008 | Burkholz et al. | |
| 2009/0006061 A1 | 1/2009 | Thukral et al. | |
| 2009/0018406 A1 | 1/2009 | Yodfat et al. | |
| 2009/0030398 A1 | 1/2009 | Yodfat et al. | |
| 2009/0036753 A1 | 2/2009 | King | |
| 2009/0043240 A1 | 2/2009 | Robinson et al. | |
| 2009/0054753 A1 | 2/2009 | Robinson et al. | |
| 2009/0063402 A1 * | 3/2009 | Hayter | A61B 5/4839 |
| 2009/0069743 A1 | 3/2009 | Krishnamoorthy et al. | |
| 2009/0069745 A1 | 3/2009 | Estes et al. | |
| 2009/0069787 A1 | 3/2009 | Estes et al. | |
| 2009/0099521 A1 | 4/2009 | Gravesen et al. | |
| 2009/0105573 A1 | 4/2009 | Malecha | |
| 2009/0131861 A1 | 5/2009 | Braig et al. | |
| 2009/0156922 A1 | 6/2009 | Goldberger et al. | |
| 2009/0156924 A1 | 6/2009 | Shariati et al. | |
| 2009/0163781 A1 | 6/2009 | Say et al. | |
| 2009/0198350 A1 | 8/2009 | Thiele | |
| 2009/0221890 A1 | 9/2009 | Saffer et al. | |
| 2009/0228214 A1 | 9/2009 | Say et al. | |
| 2009/0318791 A1 | 12/2009 | Kaastrup | |
| 2009/0326343 A1 | 12/2009 | Gable et al. | |

(56) References Cited

U.S. PATENT DOCUMENTS

| | | |
|---|---|---|
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1* | 4/2015 | Mayou ................ G09B 19/00 705/2 |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1* | 2/2016 | Morales ................ G16H 50/50 700/282 |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0336336 A1 | 11/2017 | Mastrototaro et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | OConnor et al. |
| 2019/0336684 A1 | 11/2019 | OConnor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | | |
|---|---|---|---|
| CN | 1297140 A | | 5/2001 |
| DE | 19756872 A1 | | 7/1999 |
| EP | 0341049 A2 | | 11/1989 |

(56) References Cited

FOREIGN PATENT DOCUMENTS

| | | | |
|---|---|---|---|
| EP | 0496305 | A2 | 7/1992 |
| EP | 0549341 | A1 | 6/1993 |
| EP | 1491144 | A1 | 12/2004 |
| EP | 1571582 | A2 | 9/2005 |
| EP | 0801578 | B1 | 7/2006 |
| EP | 2139382 | A1 | 1/2010 |
| EP | 2397181 | A1 | 12/2011 |
| EP | 2666520 | A1 | 11/2013 |
| EP | 2695573 | A2 | 2/2014 |
| EP | 2830499 | A1 | 2/2015 |
| EP | 2943149 | A1 | 11/2015 |
| EP | 3177344 | A1 | 6/2017 |
| EP | 3314548 | A1 | 5/2018 |
| EP | 2897071 | B1 | 5/2019 |
| EP | 3607985 | A1 | 2/2020 |
| GB | 2443261 | A | 4/2008 |
| JP | 51125993 | A | 11/1976 |
| JP | 02131777 | | 5/1990 |
| JP | 2004283378 | A | 10/2007 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 9800193 | A1 | 1/1998 |
| WO | 9956803 | A1 | 11/1999 |
| WO | 0030705 | A1 | 6/2000 |
| WO | 0032258 | A1 | 6/2000 |
| WO | 0172354 | A2 | 10/2001 |
| WO | 2002015954 | A1 | 2/2002 |
| WO | 0243866 | A2 | 6/2002 |
| WO | 02082990 | A1 | 10/2002 |
| WO | 03016882 | A1 | 2/2003 |
| WO | 03039362 | A1 | 5/2003 |
| WO | 03045233 | A1 | 6/2003 |
| WO | 2004043250 | A1 | 5/2004 |
| WO | 04092715 | A1 | 10/2004 |
| WO | 2005051170 | A2 | 6/2005 |
| WO | 2005082436 | A1 | 9/2005 |
| WO | 05110601 | A1 | 11/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066288 | A1 | 5/2009 |
| WO | 12009066287 | A3 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

International Search Report and Written Opinion for the International Patent Application No. PCT/US21/060618, dated Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/ master/lib/determine-basal/determine-basal.js [retrieved on Jun. 6, 2022] line 116-line 118, line 439-line 446.

(56) References Cited

OTHER PUBLICATIONS

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2022/012896, dated Apr. 22, 2022, 15 pages.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Continous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, dated May 16, 2017, 12 pages.

International Search Report and Written Opinion for the International Patent Application No. PCT/US2018/018901, dated Aug. 6, 2018, 12 pages.

International Search Report and Written Opinion for International Patent Application No. PCT/US2018/052467, dated Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

International Search Report and Written Opinion for International Patent Application No. PCT/US2016/063350, dated Mar. 27, 2017, 9 pages.

Extended Search Report dated Aug. 13, 2018, issued in European Patent Application No. 16753053.4, 9 pages.

International Search Report and Written Opinion for International Patent Application No. PCT/US16/18452, dated Apr. 29, 2015, 9 pages.

International Preliminary Report on Patentability dated Aug. 31, 2017, issued in PCT Patent Application No. PCT/US2016/018452, 7 pages.

International Search Report and Written Opinion for International Patent Application No. PCT/US2019/055862, dated Mar. 11, 2020.

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Searching Authority, Invitation to Pay Additional Fees, International Application No. PCT/US2006/004929, dated Jul. 27, 2006.

Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

International Search Report and Written Opinion for the International Patent Application No. PCT/US2021/016283, dated Jun. 2, 2021, 15 pages.

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Templeton et al., "Multilumen Central Venous Catheters Increase Risk for Catheter-Related Bloodstream Infection: Prospective Surveillance Study" Infection 2008; 36: 322-327.

(56) References Cited

OTHER PUBLICATIONS

Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010.
International Search Report and Written Opinion in PCT/US2008/079641 dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
R Anthony Shaw, et al., "Infrared Spectroscopy in Clinical and Dianostic Analysis." Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
International Search Report and Written Opinion for the InternationalPatent Applicationi No. PCT/US2021/018297, dated May 18, 2021, 18 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, dated May 25, 2021, 12 pages.
International Search Report and Written Opinion for the InternationalPatent Application No. PCT/US2021/017664, dated May 26, 2021, 16 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.
International Search Report and Written Opinion for the International Patent Application No. PCT/US2021/016283, dated Jun. 2, 2021, 15 pages.
International Search Report and Written Opinion for the International Patent Application No. PCT/US2021/022694, dated Jun. 25, 2021, 13 pages.
European Search Report for the European Patent Application No. 21168591.2, dated Oct. 13, 2021, 04 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.

(56) References Cited

OTHER PUBLICATIONS

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

\* cited by examiner

ONBOARDING AND TOTAL DAILY INSULIN ADAPTIVITY

TECHNICAL FIELD

The described examples provide features for a drug delivery system that enables onboarding of user data for use in a closed loop algorithm and implements adaptivity techniques to assess a user's insulin requirements on an ongoing basis using updated user data.

BACKGROUND

Diabetes management devices that operate with continuous glucose monitoring devices (CGM) and wearable insulin injection devices in an attempt to provide users with more accurate doses of insulin are available. The wearable insulin injection devices are typically replaced after a number of days, if functioning properly. Upon replacement of the wearable insulin injection device, the diabetes management algorithm executing on the diabetes management devices may require a user to provide the insulin dosing inputs (referred to as "open-loop" operation) to the algorithm while the algorithm collects data over a period of time, such as days or weeks, for the diabetes management device to be able to begin an automated insulin dosing regimen (referred to as "closed loop" operation). As a result, a user may have to manually provide insulin dosing inputs while the diabetes management device is in open-loop operation for several days or weeks before closed-loop, automated insulin delivery operation may begin.

The delay in beginning an automated insulin dosing regimen that is part of closed-loop operation is inconvenient to users and also limits the diabetes management device to only providing an accurate estimate of a user's true insulin needs for a short time before the wearable insulin injection device has to be replaced again and repeating the cycle of open-loop and closed-loop operation.

SUMMARY

An example of a non-transitory computer readable medium that is embodied with programming code executable by a processor is disclosed. The processor when executing the programming code is operable to perform functions, including functions to retrieve a portion of an insulin delivery history related to a user. The processor when executing the programming code may be operable to determine whether the portion of the insulin delivery history meets sufficiency requirements. In response to a determination that the insulin delivery history meets the sufficiency requirements, an upper safety boundary may be selected as a limit for an amount of insulin to be delivered for a period of time. The selected upper safety boundary may be a greater amount of insulin than an amount of insulin associated with a lower safety boundary. The amount of insulin to be delivered for a period of time may be set that is below the selected upper safety boundary. Delivery of an amount of insulin may be initiated according to the set amount of insulin.

Disclosed is a device including a processor, a memory, and a transceiver. The memory may be operable to store programming code, an artificial pancreas application, onboarding application code, adaptivity application code, and data related to the artificial pancreas application, the onboarding application code, and the adaptivity application code. The transceiver may be communicatively coupled to the processor and be operable to receive and transmit signals containing information usable by or generated by the artificial pancreas application, the onboarding application code, or the adaptivity application code. The programming code, the artificial pancreas application, the onboarding application code, and the adaptivity application code may be executable by the processor. The processor when executing the artificial pancreas application, the onboarding application code, or the adaptivity application code, is operable to control delivery of insulin, and to perform functions. The functions include retrieving a portion of an insulin delivery history related to a user. The insulin delivery history may include an amount of insulin delivered for each of a number of insulin delivery dosages administered to the user. The processor may determine whether the portion of the insulin delivery history meets insulin history sufficiency requirements. In response to a determination that the insulin delivery history meets the insulin history sufficiency requirements, an initial total daily insulin value may be set. Transmit the initial total daily insulin value for receipt by the wearable drug delivery device.

DETAILED DESCRIPTION

Figure 1:
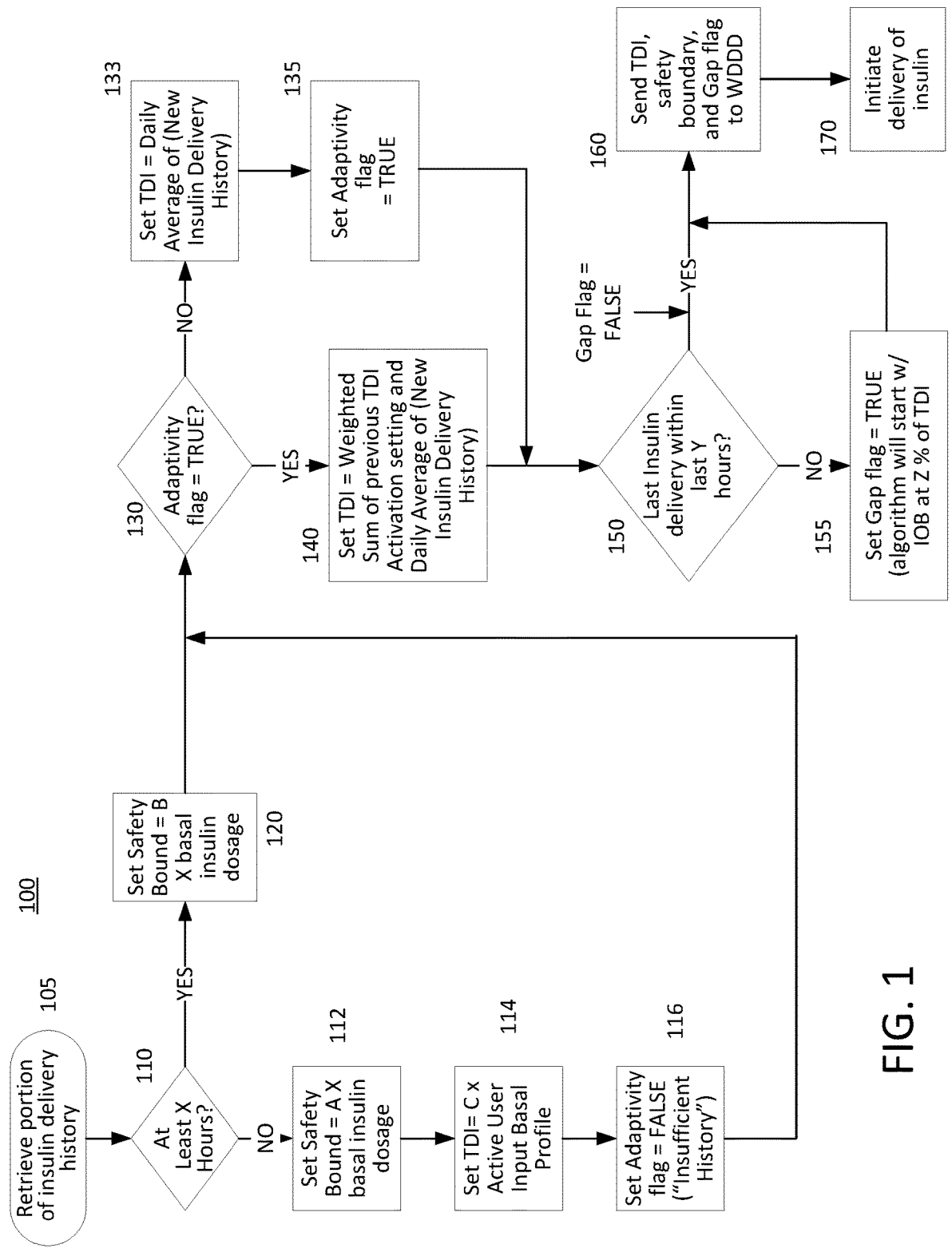
FIG. 1 shows a flow chart of an example process for determining insulin delivery system settings.

Various examples provide a method, a system, a device and a computer-readable medium for facilitating condensed onboarding of a user insulin therapy program and/or an adaptivity scheme that is operable to determine an accurate estimate of the insulin needs of a user of any generic insulin delivery system. For example, the estimate of the user's captured as the user's insulin needs may be based on a total daily insulin (TDI) parameter of the particular user. An example process also enables a reasonable "onboarding" scheme to provide a starting estimate of the TDI and reasonable limits of maximum confidence if there is insufficient history of insulin delivery.

Some insulin delivery systems may keep track of past insulin delivery history. For example, the stored past insulin delivery history may keep track of when dosages of insulin are administered, an amount of insulin in the dosage, a type of insulin administered (e.g., fast acting, regular, intermediate-acting, long-acting or the like), blood glucose measurements, and the like. Using the insulin delivery history, the described examples provide methods for total insulin delivery assessment within an automated insulin delivery system that reduces the risk of hyperglycemia and hypoglycemia using the insulin delivery history over increasingly longer history time horizons. Since nearly all insulin delivery is typically known to an insulin delivery system over time with high accuracy, the examples described herein provide an assessment of total insulin delivery using known insulin delivery history to determine each user's total daily insulin (TDI) needs more accurately when initiating a new drug delivery device and while the drug delivery device is operating.

Due to the accuracy of the described algorithms, the described examples enable receding insulin delivery history time horizons and minimum valid insulin delivery history lengths, as well as maximum differences between timestamps of the first and last entries of an insulin delivery history of sufficient duration that are utilized to generate a TDI parameter that is a robust, generalizable TDI estimate for a particular user. An example process is operable to calculate this TDI parameter may dynamically update the TDI estimate over time based on long term changes to the user's physiology. The example method may be robust enough to respond to any short-term, acute variations in insulin sensitivities which may occur due to temporary life events, such as sickness, rapid weight loss, intense exercise regimen, or the like.

The process examples may be used with any additional algorithms or computer applications operable to manage blood glucose levels, insulin delivery, and general overall insulin therapy. Such algorithms may be referred to as an "artificial pancreas" algorithm-based system, or more generally, an artificial pancreas (AP) application. An AP algorithm is operable to provide automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dl to 120 mg/dl, which is a range satisfying the clinical standard of care for treatment of diabetes. However, an AP application enhanced by the method and processes described herein may be able to establish insulin dosages more precisely and timing for administering the established insulin dosages. As described in more detail with reference to the examples of FIGS. 1-7, the AP application may utilize insulin delivery history and other information to generate and send a command to a wearable drug delivery device including, for example, a pump, to control delivery of a determined dose of insulin to the user, change the amount or timing of future insulin doses, as well as to control other functions.

The described examples are advantageous and are beneficial to any application of a "closed loop" processing algorithm or automated insulin delivery mechanisms, allowing a substantially immediate and safe initiation of automated delivery at first pod use, while also allowing the delivery mechanism to match any changes in the user's insulin needs over time.

The described processes may be particularly advantageous when a user is first using or replacing a wearable drug delivery device, such as an OmniPod® (Insulet Corporation, Billerica, MA) or a similarly configured device with similar capabilities. These wearable drug delivery device are capable of administering doses of insulin for several days, but for ease of discussion, the number of days that the wearable drug delivery device may be used may be limited to three days. In addition, whether the user is first using a new wearable drug delivery device, or replacing an expended wearable drug delivery device, the installation of the new wearable drug delivery device or installation of the replacement wearable drug delivery device, the installation of the wearable drug delivery device (new or replacement) may be referred to as an initial installation or a first installation.

Figure 7:
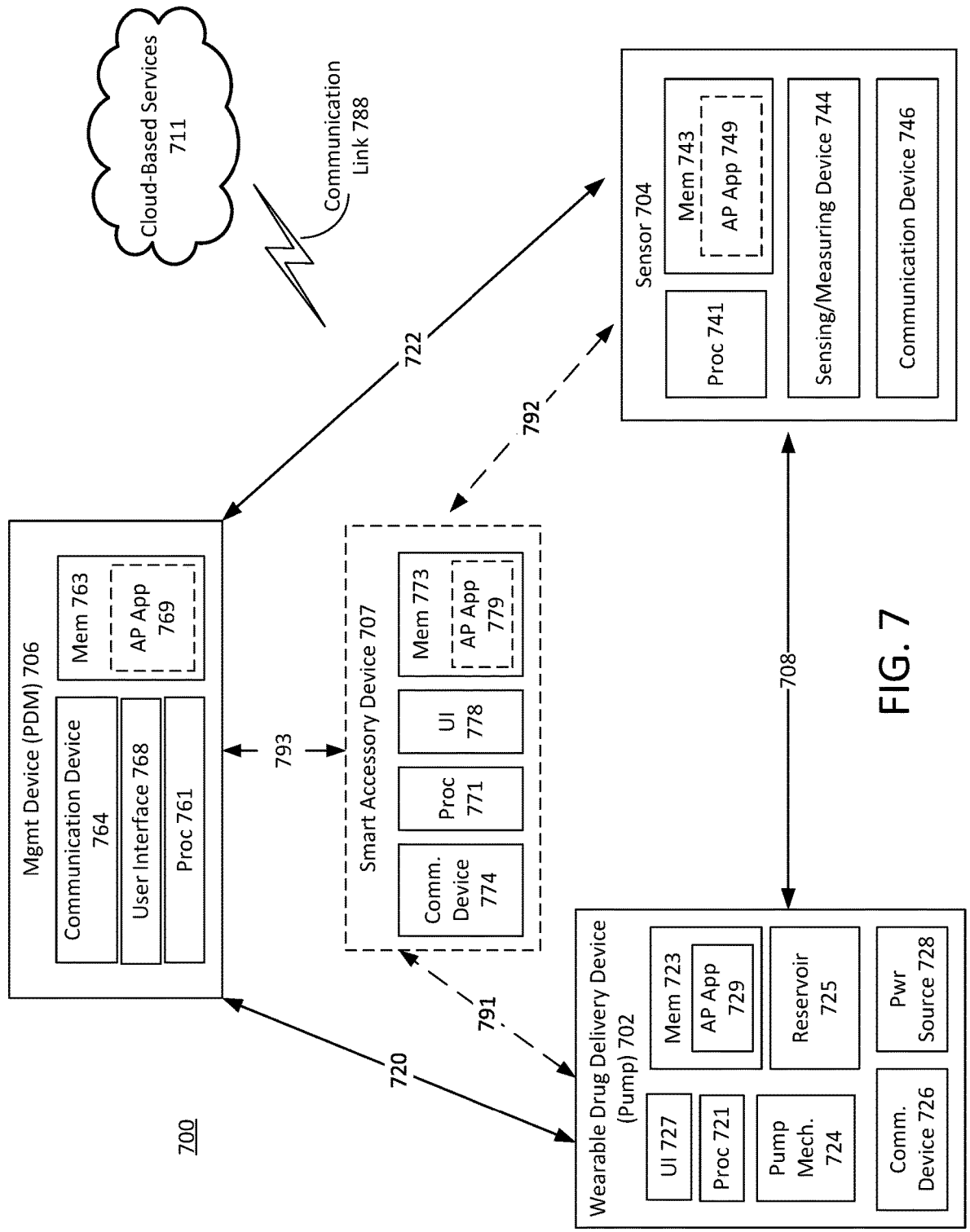
FIG. 7 illustrates a functional block diagram of drug delivery system suitable for implementing the example processes and techniques described herein.

As described later in more detail with reference to FIG. 7, the wearable drug delivery device may be controlled by a processor that executes the AP algorithm discussed above and that may also be operable to execute the example processes described herein. The processor may be configured to be a component of a mobile device, such as smartphone, a dedicated insulin therapy program processor, a tablet, a smart wearable device (e.g., a smart watch, a smart fitness device or the like) or other type of mobile device. Alternatively, or in addition, the processor may also be part of the wearable drug delivery device or another device operable to communicate with wearable drug delivery device.

In the examples, a process referred to as onboarding may be performed based on an availability of a sufficient insulin delivery history at the initial or first installation of the wearable drug delivery device for treatment of a user. The onboarding process may be a process by which a processor may receive user parameters to control the wearable drug delivery device to provide automated insulin delivery. In an example, user parameters may include blood glucose measurements, doses (i.e., dosage amounts) of administered insulin, times when insulin is administered, carbohydrate-to-insulin ratio, insulin sensitivity rating, insulin adjustment factor, basal profile, or the like. As a note, a basal profile may be a 24-hour profile of basal needs defined by start-end times and basal delivery rates for each interval. For example, one basal profile may be:

| Time Segment | Basal Quantity |
|---|---|
| 0:00-8:00 | 0.9 U/h |
| 8:00-16:00 | 1.5 U/h |
| 16:00-24:00 | 1.2 U/h |

A "basal profile" refers to the entire table above. Different users may have different basal profiles depending on their individual needs.

The onboarding process may be abbreviated if a sufficient insulin delivery history is available and accessible. Examples of onboarding procedures may include a process to reset total-daily-insulin (TDI) estimates when the insulin delivery history is insufficient given sufficiently long gaps in insulin delivery history for a user.

In another process example, the user parameters used during onboarding to establish insulin delivery system settings that start automated insulin delivery may be adapted over time by a process implemented when the processor enters adaptivity mode. The processor may initiate an adaptivity mode when it is determined that sufficient during which the system adjusts performance over time based on new information including delivery of insulin, new blood glucose measurements, or the like. The insulin delivery system settings may be updated by calculating updated parameters based on the new information and the received user parameters.

The combination of the onboarding process and the adaptivity process during the application of any "closed loop" or automated insulin delivery mechanisms allows for an immediate and safe initiation of automated delivery at first pod use (i.e., while also allowing the delivery mechanism to match any changes in the user's true insulin needs over time.

FIG. 1 shows a flow chart of an example process for determining insulin delivery system settings. The process 100 may be performed by a processor operable to control a wearable drug delivery device over a period of time. For example, at 105, a portion of an insulin delivery history related to a user may be retrieved from data storage, such as a memory of the processor, a remote server, such as a cloud-based data storage system, or the like. At 110, the processor may determine whether the portion of the insulin delivery history meets sufficiency requirements. The assessment for a sufficient history at 110 of the onboarding process may be executed at a standard time during which the user would typically interact with the wearable drug delivery device and/or with a personal diabetes management device (described in more detail with reference to FIG. 7). In one example, such as a typical tubed pump drug delivery device, this assessment at 110 may occur each time the user replaces an insulin container within the insulin management and delivery system (not shown in this example). In the example, at 110, the processor may analyze the retrieved portion of the insulin delivery history for predetermined criteria that, if present, satisfy the insulin delivery history sufficiency requirements. For example, an analysis of the portion of the insulin delivery history by a processor may determine whether there is sufficient history to execute adaptivity or onboarding and perform a safe onboarding process for a user when sufficient insulin delivery history is not available (i.e., the insulin delivery history is insufficient).

The process at 110 of FIG. 1 may be summarized as, the following conditions can be assessed to ensure that any TDI estimates cover a sufficient duration and sufficient sample of insulin needs across all hours of the day: 1) the system may have at least a variable $MIN_{length}$ hours of known insulin delivery history; 2) the known insulin history of $MIN_{length}$ or more may span a period of no more than $MAX_{block}$ hours total; and 3) the known insulin delivery history that meets the first two conditions may not be older than $MAX_{history}$ days.

In one exemplary example, $MIN_{length}$ hours can be set to 48, or at least two days of insulin delivery history. $MAX_{block}$ hours can be set to 54 hours, or 2.5 days of max span. $MAX_{history}$ can be set to 30 days, or that the considered insulin delivery history cannot be older than 30 days.

The design of the minimum length of hours $MIN_{length}$ is utilized to ensure there is sufficient data to calculate a reasonable estimate of the TDI. The design of maximum span of this data $MAX_{block}$ is utilized to ensure that the available data isn't overly weighted to a certain period of the day—for example, an assessment of the user's insulin needs that only span the breakfast post prandial period of 8 am-12 pm over 12 days will provide 48 hours of data but may not be representative of the user's true insulin needs. Finally, the design of maximum age of insulin delivery history $MAX_{history}$ is implemented to ensure that the system reassesses insulin delivery history if any long term changes in insulin needs is not captured due to significant gaps in the known insulin history.

An example of an insufficient insulin delivery history may be when there are long gaps in insulin delivery history for a user. Long gaps in the insulin delivery history may be considered gaps of longer than 2 to 8 hours, for example, in a 48-hour period or a 48-hour period of time that is older than 30 days old. Of course, other gaps may also be considered long, such as 9 hours in a 36 hour time period, 2 hours in a 24 hour time period, 15 minutes in a 1 hour time period, or the like.

In addition, in certain examples, this insulin history assessment can also consider short term gaps in insulin history less than 30 days. In these certain examples, the processor may account for the possibility of unknown insulin delivery history during these gaps and execute its calculations assuming a fixed or variable value of insulin may have occurred as insulin-on-board, or IOB. In one example, this extra insulin delivery $IOB_{extra}$ can be set to ⅙th of the TDI, to represent one standard meal (½ of TDI is generally attributed to meal boluses, and the user generally takes 3 meal boluses per day).

Returning to the example of FIG. 1, in response to a determination at 110 that the insulin delivery history meets the sufficiency requirements, the processor may generate based on a result of the analysis, a confirmation signal confirming that the insulin delivery history meets the sufficiency requirements that satisfies a total number of hours of data within a contiguous period of time falling within a previous number of days, and the process 100 proceeds to 120. In certain examples, onboarding and adaptivity process can be paired with an automatic insulin delivery algorithm, and reduce the constraint on maximum insulin delivery possible by the algorithm. At 112, this limit may be set using a multiplier A can be "2 times" the basal insulin limit, in certain examples, which is a reduction from a multiplier B times, which may be "4 times" the basal insulin limit given sufficient history, and as set at 120.

For example, based on the determination at 110, the processor may limit an amount of total daily insulin to be administered by the wearable drug delivery history to a multiple of a basal insulin dosage set by a user. For example, a first multiplier of the basal insulin dosage, such as B (which may equal 4, 6 or 8), may be selected if the processor determines the insulin delivery history is sufficient, while a second multiplier, such as A (which may be set to 1.5, 2 or 3), may be selected if the processor determines the insulin delivery history is insufficient. In the example of sufficient insulin delivery history, the basal input limit may be set as 4 times the basal insulin dosage, while for an insufficient insulin delivery history the basal input limit may be set as 2 times the basal insulin dosage.

At 120, the processor may select an upper safety boundary for an amount of insulin to be delivered for a day, such as a total daily insulin, or the like. For example, the selected upper safety boundary may be a as the multiplier B times a basal limit between a maximum amount of insulin for delivery and a minimum amount of insulin to be delivered by the drug delivery device. The value B may be a multiplier that is applied to an amount of insulin that is to be delivered for a period of time. For example, the value B may be in an approximate range of 3.5-5.0, or a specific value such as 4, or the like. In an example, the period of time during which the value B may applied may be hours, a day, a number of days, such as two or three, an amount of time associated with a lifecycle of a drug delivery device, or the like.

Conversely, if processor determines at 110 that the insulin delivery history does not meet the sufficiency requirements (e.g., the total number of hours does not meet the required total hours (e.g., 48 hours), has too long of a gap (e.g., greater than 2-8 hours) and is older than required age of the data (e.g., greater than 30 days old)), the processor may trigger an onboarding mode to minimize any risk to the user. In the onboarding mode, the process 100 may proceed from 110 to 112. At 112, the processor may be operable to select a lower safety boundary for an amount of insulin to be delivered in response to a determination that the insulin delivery history fails to meet the sufficiency requirements. The time period during which insulin may be delivered at the lower safety boundary may be for a day (i.e., 24 hours), twelve hours, eight hours or the like. The selected lower safety boundary is lower than the selected upper safety boundary and greater than a minimum amount of insulin to be delivered by the drug delivery device. The value of the lower safety boundary may be a multiplier having a value A that may be multiplied to the user's TDI based basal to limit the maximum insulin delivery to be lower than under standard use. This value A may be selected to improve user safety while still allowing delivery of sufficient insulin to maintain normal daily blood glucose fluctuations. For example, the selected lower safety boundary maybe less than the selected upper safety boundary and greater than a minimum amount of insulin to be delivered by the drug delivery device. Due to the lack of sufficient insulin delivery history in the example, an initial amount of insulin to be delivered upon installation of the drug delivery device may be set.

The amount of insulin set to be delivered for the day may be set below the selected lower safety boundary (114). During the onboarding process, the system utilizes user input basal parameters to calculate the TDI. For example, the AP algorithm may provide an average of the user's basal insulin input for use by the onboarding process. For example, if the user's basal insulin input may be 0.6 units of insulin/hour in the morning, 1.2 units of insulin/hour afternoon and 0.8 units of insulin/hour in the evening and night. The algorithm is operable to use the average of the user's basal insulin for a 24 hour period. Insulin needs do not change significantly overtime. For example, a teenager's insulin dosages may only change 20% within a year. In a specific example, the TDI is calculated by the sum of each user input basal segment (weighted by the duration of each basal segment, which is typically defined as the difference between the start time of the basal segment and end time of the basal segment) multiplied by 2, as in the following equation 1:

$$TDI_{onboarding} = 2\Sigma b(t)*(t_{b,end} - t_{b,start}) \qquad \text{Eq. 1}$$

wherein, b(t) is a user input basal segment, $t_{b,start}$ is the time (in hours or fractions thereof) that the basal segment begins and $t_{b,end}$ is the time (in hours or fractions thereof) that the basal segment ends, and 24 represents hours in a day. This onboarding TDI is then used to guide any manual or automated insulin delivery to the user, with the possibility of an additional safety flag that can be set to indicate to the system that the TDI estimate is based on insufficient history, and that the system is less confident about the accuracy of this system.

For example, the processor may set, at 114, a total daily insulin for the lower safety boundary using a current active user input basal profile for delivery of insulin times a multiplier associated with the lower safety boundary. The multiplier may have a value C, which may be in an approximate range of 1.2-3.5, or the like. In an example, the period of time may be hours, a day, a number of days, such as two or three, an amount of time associated with a lifecycle of a drug delivery device, or the like.

After the total daily insulin is set based on the lower safety boundary at 114, the processor may indicate that there is insufficient insulin delivery history (116). For example, the processor may set an adaptivity flag to false or untrue, which indicates to processes other than process 100 that there is insufficient insulin delivery history for adaptivity mode and/or related functions.

After the performance of either step 116 or step 120, the process 100 may lead to decision step 130. At 130, the processor may decide based on new information related to an amount of insulin delivered by the drug delivery device retrieved from an updated insulin delivery history of whether an adaptivity mode of the processor is active or inactive. For example, the processor may determine the adaptivity flag is set to true. In which case, based on a result of the determination, the processor may retrieve new information related to an amount of insulin delivered by the wearable drug delivery device from an updated insulin delivery history. For example, the new information may be information collected since the insulin delivery history was retrieved at step 105. In an example, the processor may set, or reset (in the case of an insufficient insulin delivery history), the total daily insulin (140) based on the new information.

For example, assuming that the insulin delivery history is determined to be sufficient, the upper safety boundary may be selected, and the adaptivity flag is set to TRUE, the total daily insulin may be set (at 140) to an amount of insulin to be delivered for a period of time based on a weighted sum of a previously set total daily insulin and, from the new information, the daily average of the amount of insulin delivered during the waiting period (e.g., based on the updated insulin delivery history). The weighting may, for example, be in percentages, such as 80:20, 60:40, 50:50) or the like, depending upon conditions related to the insulin delivery history, blood glucose measurements that are more recent than the insulin delivery history, or the like. Of course, other weightings may be used, or even cost functions or the like may also be implemented to set a new total daily insulin setting.

Alternatively, at 130, the processor may determine that the adaptivity flag is not set to TRUE (i.e., the adaptivity flag is set to FALSE) in which case, the process 100 proceeds to 133. At 33, the total daily insulin may be set to an amount of insulin to be delivered for a period of time based on a daily average of the amount of insulin delivered during the waiting period. After 133, the process 100 proceeds to 135 at which the processor sets the adaptivity flag to TRUE, and the processor initiates an adaptivity mode.

After either step 140 or step 135 is performed, the process 100 proceeds to 150. At 150, a determination is made whether a last insulin delivery was made within the last Y hours. In this example, Y is a time value that may have a value in minutes or hours, such as 6 hours, 120 minutes, or the like. For example, the wearable drug delivery device may be operable to provide acknowledgment signals to the processor in response to receipt of an actuation signal or that a dose of insulin was delivered. Alternatively, the wearable drug delivery device may transmit a signal whenever insulin is delivered by a pump controller coupled to a pump mechanism of the wearable drug delivery device. In this example, the pump controller may not have provided the acknowledgment that a drug delivery was made or may provide some indication of a failure to deliver insulin by the drug delivery device (e.g., there is no insulin available, a reservoir is empty, the pump mechanism failed, or the like).

In an example, in response to a determination that a last insulin delivery was not made within the last Y hours the process 100 may proceed to 155. At 155, a gap flag may be set to TRUE, which may mean that a gap exists that makes the insulin delivery history (now including any updated or new data) insufficient. In addition, in response to a determination that an insulin delivery was not made within the predetermined last insulin delivery time period, the processor may establish a starting insulin on board (IOB) setting equal to a percentage of the set total daily insulin dosage. This is also a safety constraint to ensure that too much insulin is not delivered to a user based on calculations performed by the processor executing an AP algorithm and the adaptivity and onboard programming code. This IOB may not be included in the insulin delivery history to ensure that the TDI calculations in the rest of the onboarding and adaptivity process are not impacted. After step 155, the process 100 proceeds to 160.

Conversely, in response to a determination at 150 that a last insulin delivery was made within the last Y hours, the process 100 proceeds to 160.

At 160, the processor may send, via a wired or wireless connection established with a wearable drug delivery device, a set total daily insulin dosage, a selected safety boundary setting, and a gap flag setting to the wearable drug delivery device (WDDD). From 160, the process 100 may proceed to 170.

At 170, the processor may initiate delivery of an amount of insulin according to the selected upper safety boundary. For example, the processor may transmit a signal via the connection established with a wearable drug delivery device that causes the actuation of a mechanism of the wearable drug delivery device to deliver an appropriate amount of insulin to a user. The appropriate amount of insulin being a dose related to the set total daily insulin or less than the selected upper safety boundary.

After 170, the process 100 may proceed back to 105 until another pod is ready for activation.

In certain examples, the process 100 may provide for different settings within the AP application or algorithm based on the sufficiency of the insulin delivery history. In a first example, when an initial pod is activated and the insulin delivery history is insufficient (step 110), the AP application may set the safety bound at A times the basal input dosage (step 112), the TDI may be set to the active user input basal profile (114), and, the adaptivity is set to FALSE (step 116) at activation. In another example, a first pod being activated that has access to a sufficient insulin delivery history (step 110), may have different settings than this first pod based on the process 100. For example, the settings for the next pod may have a safety bound set to B times the basal insulin dosage (120), the adaptivity flag may be set to FALSE at activation (as this may be a default value, a setting carried over from the previous pod (the first pod), or the like)(step 130), and the TDI may be set based on the previous pod's usage. For a second pod and subsequent pods that have sufficient insulin delivery history that follow the first pod may have a safety boundary set to B times (e.g., 4 times, in some examples) the basal input dosage, the TDI may be set to be a weighted sum ($1^{st}$ weight X previous pod usage+$2^{nd}$ weight X previous pod activation TDI setting), and an adaptivity flag set to TRUE. For any pod, once activated, the TDI parameter upon which the AP application operates may not change during the lifecycle of the pod. However, the pod's actual TDI measured by insulin delivered and reflected in the insulin delivery history, may differ from the TDI set during activation of the respective pod. Hence, a weighted sum of the TDI measured and TDI activated, is used to activate the subsequent pod, when the activity flag is set to TRUE.

Figure 2:
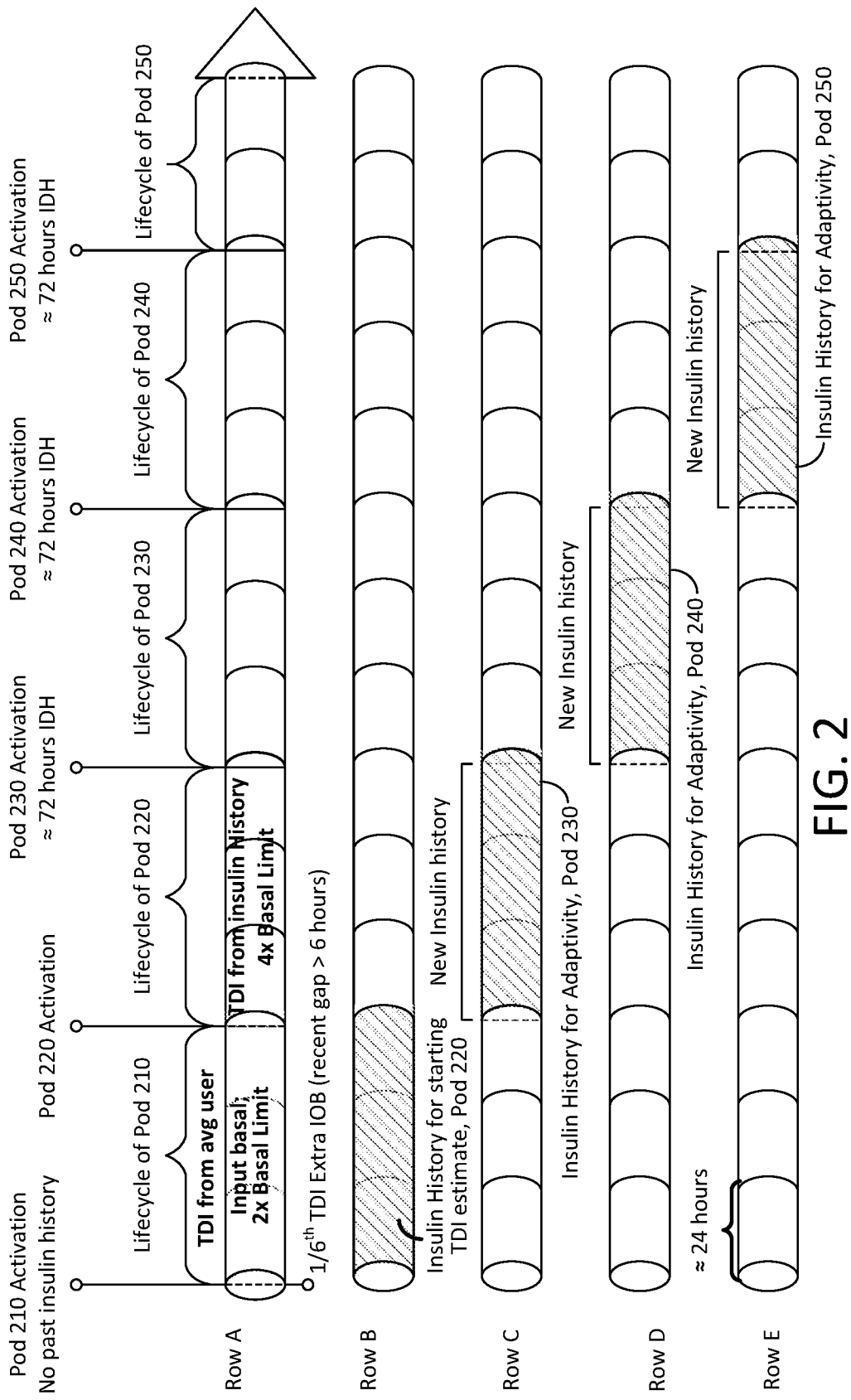
FIG. 2 shows a graphic illustrating an example process related to an example situation related to use of a wearable drug delivery device.

It may be helpful to describe details of the onboarding process and adaptivity process with reference to the FIGS. 2-6. In the example of FIG. 2, the process 100 may be executed by a processor of a personal diabetes management device, a smart accessory device, a drug delivery device, or the like (or by a distributed processing configuration between the various devices) whenever the wearable drug delivery device is replaced.

The onboarding process and adaptivity process, for example, may be conducted automatically with no or limited user interactions by the processor or pod at each "pod activation" (the term "pod" as used herein is equivalent to a wearable drug delivery device and the terms are used interchangeably). For example, at the activation of pod 210, there is no past or previous history (neither short term history nor long term history in this example) so the insulin delivery history is determined at 110 of FIG. 1 to be insufficient. In response to the determination that the insulin delivery history is insufficient for the initial settings of pod 210, the onboarding logic (executing on a processor) may initiate process 100, steps 112-116, of FIG. 1. For example, at pod 210 activation (Row A), a determination by the processor that there is an insufficient insulin delivery history results in a closed loop algorithm executed by a processor that limits a total insulin to be delivered at any one cycle, which may be 1, 5, 10, 15 minutes or the like, to no greater than C times (or "2×" as shown in the example of FIG. 2 and equation 1) the average of a user's input basal profile. Further, in this example, the processor additionally add $\frac{1}{6}^{th}$ of the user's total daily insulin, estimated as 2 times the sum of the user's basal profile as in equation 1, as starting insulin on board to further limit insulin delivery since there is a recent gap in the insulin delivery history of greater than 6 hours. Of course, other fractions or percentages of total daily insulin or basal insulin delivery may be chosen or set. This setting may be used for the lifecycle of pod 210 (e.g., approximately 3 days or the like). After the lifecycle of pod 210 expires, another pod, such as pod 220, may be activated. As part of the activation of pod 220, the processor may retrieve the insulin delivery history of pod 210. As shown in Row B, the insulin delivery history of pod 210 may span approximately 72 hours (of insulin delivery history (IDH)) without any gaps. As a result, the processor may assess the insulin delivery history to be sufficient. As a result of the determination that the insulin delivery history is sufficient, the processor may set safety boundary of the total daily insulin that may be delivered to be B times (or as shown in this example, four times (4×)) the basal insulin delivery limit for the day.

Pod 220 may reach the end of its lifecycle, and during the activation of pod 230, the processor may retrieve the new insulin delivery history of pod 220. Using the new insulin delivery history of pod 220, the processor may set the safety boundary to B times the total daily insulin (TDI). In the example of FIG. 2, each of pods 230, 240 and 250 accumulate sufficient insulin delivery histories and may be activated using the safety boundary set to B times the total daily insulin (TDI).

Figure 3:
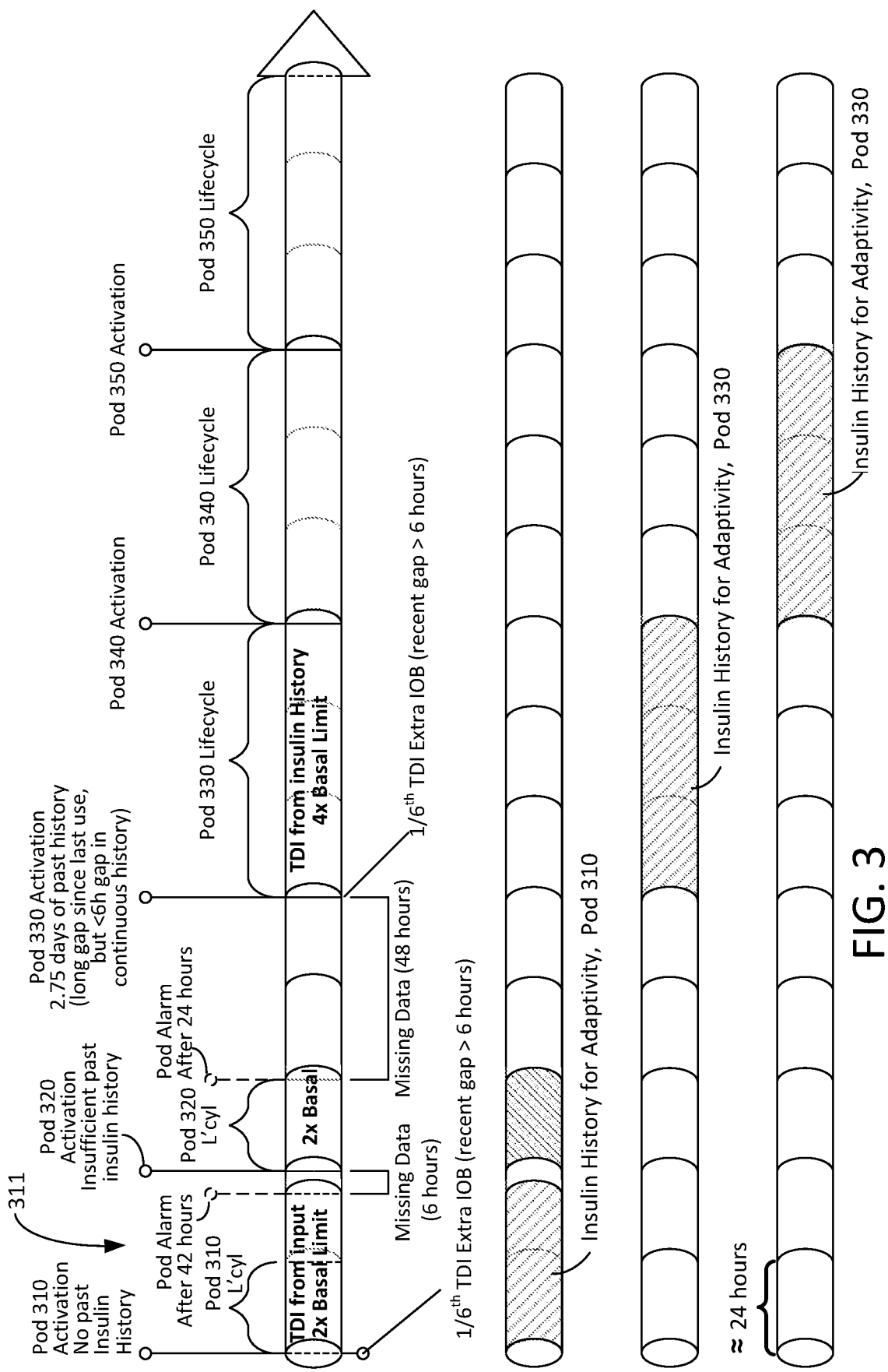
FIG. 3 shows a graphic illustrating a further example process related to another example situation related to use of a wearable drug delivery device.

In the example of FIG. 3, the assessment of the insulin delivery history may reveal during activation of each new wearable drug delivery device that the insulin delivery history is insufficient, for example, the insulin delivery history may be less than a threshold number of hours, such as 48 hours, for example. Since the insulin delivery history of pod 310 in the example of FIG. 3 does not reach the threshold number of hours number of hours, the pod 310 activation may set the insulin on board at a percentage or fraction of the total daily insulin. In the example of FIG. 3, due to a gap in the insulin delivery history greater than 6 hours, the processor may be operable to establish settings of the pod 310 for the insulin on board at $\frac{1}{6}^{th}$ of the total daily insulin. In addition, the safety boundary may be set at A times the basal insulin limit, or in this example, at 2 times the basal insulin limit.

When operating properly, the processor (not shown in this example) may, for example, send control signals to the pod 310 instructing the pod 310 to deliver a dose of insulin. In response to delivering the dose of insulin, the pod 310 may generate an acknowledgment signal that is sent to the processor.

In the example, at 311, the pod 310 may become defective, may run out of insulin, or experience another failure that results in non-delivery of insulin, and may only be used for 42 hours (2 days). In response to the failure, the pod 310 may, for example, be operable to generate an alarm or other indication that insulin is not being delivered and may forward an alarm signal to the processor. The processor may be operable to indicate an alarm condition in the event the acknowledgment signal is not received within a predetermined time period or the like. In an example, although insulin is being delivered, a transceiver in the pod 310 may have lost connectivity with the processor, or some other communication failure. The pod 310 and/or the processor may be operable to track how long the alarm has been set in order to determine whether the insulin delivery history is sufficient.

Upon the activation of pod 320, the processor may be operable to determine that there is insufficient insulin delivery history due to the gap of 6 hours. As a result, at the pod 320 activation, due to the gap in the insulin delivery history greater than 6 hours, the processor may establish settings for the insulin on board at $\frac{1}{6}^{th}$ of the total daily insulin and the safety boundary is set at 2 times the basal insulin limit. The pod 320 may provide data for approximately 24 hours during which the pod 320 may be operating properly and delivering insulin according to pod settings indicated by the processor. Of course, the pod 320 may be defective or may be removed from the user. As a result, in this example, the collection of insulin delivery history data may again fail so there is insufficient insulin delivery history at the end of the pod 320 lifecycle.

The pod 330 activation is an example of the improvements and sophistication of the onboarding examples. In the example, at the time of the pod 330 activation, the processor may be operable to determine that the insulin delivery history is approximately 2.75 days or 68 hours out of 72 hours, without a gap greater than 6 hours (recall the gap in pod 310 is 6 hours) and the insulin delivery history is less than 30 days old (i.e. 48 hours (or 2 days) since last data was collected and 72 hours (or 3 days) since the continuous collection of insulin delivery history data. Based on this information, the processor may be operable to determine that the insulin delivery history is sufficient and may set the safety boundary at B times the basal insulin limit, or, in this example, at 4 times the basal insulin limit. However, since the last insulin delivery has been beyond Y hours, such as 6 hours in this example, the gap flag may be set to TRUE and the insulin on board is set to a percentage or fraction of the total daily insulin, such as $\frac{1}{6}^{th}$ or the like. The flexibility of the proposed adaptivity approach means that this additional insulin on board during the beginning of each pod session can be utilized to limit the algorithm behavior without impacting the estimate of total daily insulin requirements. For example, pods 340 and 350, due to sufficient insulin history, may all begin operation in adaptivity mode (e.g., insulin history for adaptivity, pod 330, etc. as shown in FIG. 3 is evaluated for pod 340 activation).

In the example of FIG. 3, pod 330 operates continuously without a lapse in insulin delivery history data as do pods 340 and 350, which are activated in a manner similar to pod 330 according to the process example shown in FIG. 1.

Figure 4:
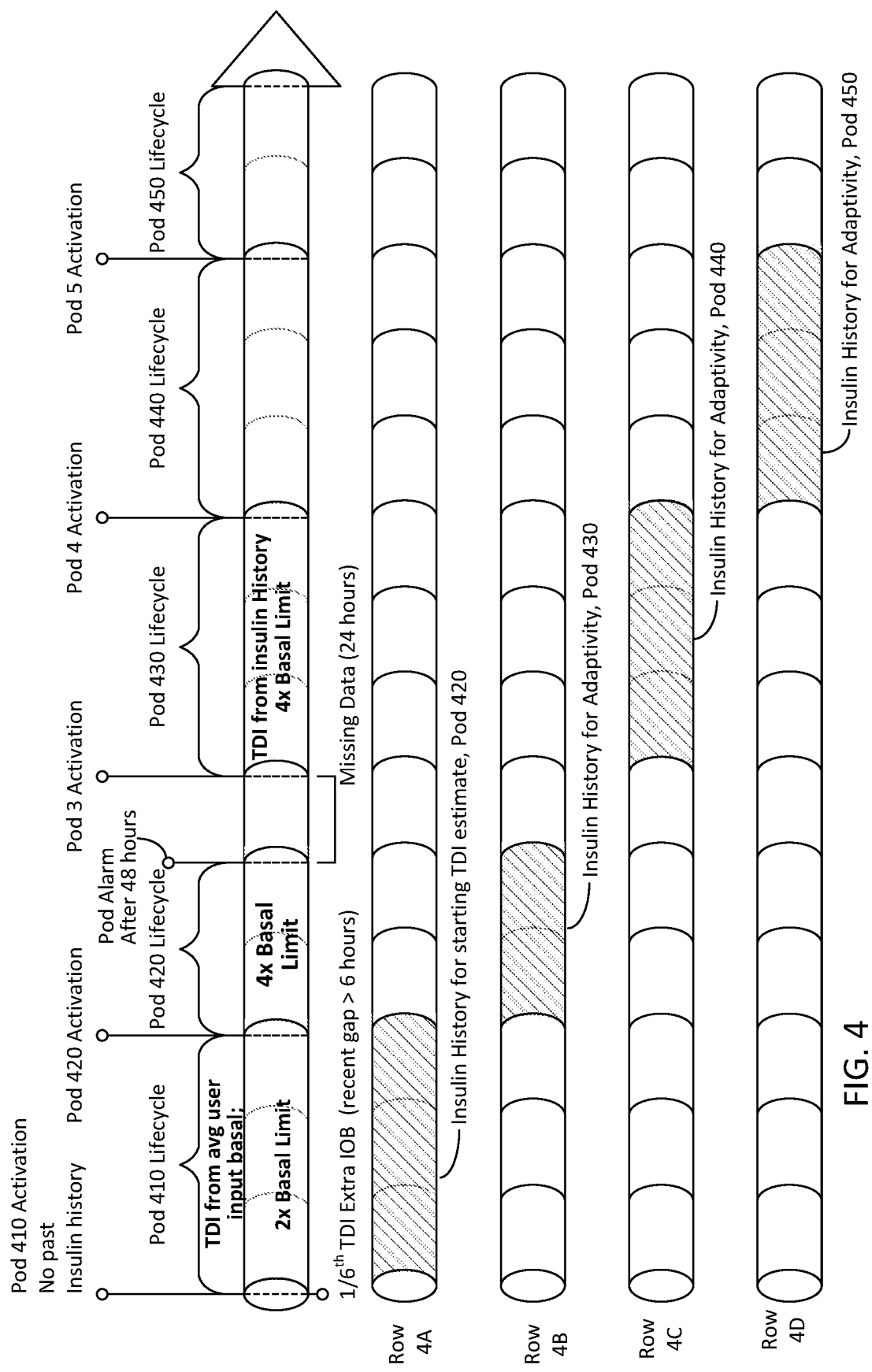
FIG. 4 shows a graphic illustrating another example process related to a further example situation related to use of a wearable drug delivery device.

The example of FIG. 4 illustrates another example process. In the example of FIG. 4, during the activation of pod 410, the processor may be operable to note that there is insufficient insulin delivery history. As a result, in the example of FIG. 4, the processor may be operable to establish settings of the pod 410 for the insulin on board at $\frac{1}{6}^{th}$ of the total daily insulin. In addition, the safety boundary may be set at A times the basal insulin limit, or in this example, at 2 times the basal insulin limit.

As shown in row 4A, the pod 410 operates and provides data for its entire lifecycle. At the end of the lifecycle of pod 410, it is time to replace pod 410 with pod 420. At the activation of pod 420, the processor may be operable to determine that the insulin delivery history provided during the lifecycle of pod 410 is sufficient, and, as a result, may set the safety boundary of pod 420 at B times the basal insulin limit, the adaptivity flag may be set to FALSE and set the total daily insulin as a daily average of insulin delivered according to a new insulin delivery history of pod 410 (as shown in Row 4A—Insulin History for starting TDI estimate, Pod 420).

The lifecycle of pod 420 is cut short, and the processor or pod 420 may generate an alarm. As a result of the shortened lifecycle of pod 420, the insulin delivery history, as shown in Row 4B, is missing data from the most recent 24 hours (as shown at 421). The time period (i.e., 24 hours) of missing data may be greater than the threshold Y time (e.g., 6 hours) for missing data (as evaluated at 150 of FIG. 1). The processor may be operable to determine that while there is a gap greater than 6 hours but with data less than 30 days old, the insulin device history is sufficient because there is a continuous 48 hours of uninterrupted insulin delivery history data. As a result, the processor may be operable to set the total daily insulin based on the insulin delivery history and set the safety boundary at B time basal insulin limit but limit the starting insulin on board at a percentage or fraction of the insulin on board. For example, the processor may be operable to set the insulin on board at $\frac{1}{6}^{th}$ or the like of the total daily insulin.

Since the pod 430 generates insulin delivery data for its entire 72 hour (or 3 day) lifecycle and provides a sufficient insulin delivery history (as shown in Row 4C), the activation of pod 440 is straightforward including the setting of the adaptivity flag to TRUE for pod 440. Likewise, the lifecycle of pod 440 is completed with a sufficient insulin delivery history without any gaps (as shown in Row 4D), so the activation of pod 450 is straightforward including the setting of the adaptivity flag to TRUE for pod 450. Pods 430, 440 and 450 may all begin operation in adaptivity mode (e.g., insulin history for adaptivity, pod 430, etc. as shown in FIG. 4) due to sufficient insulin history.

Figure 5:
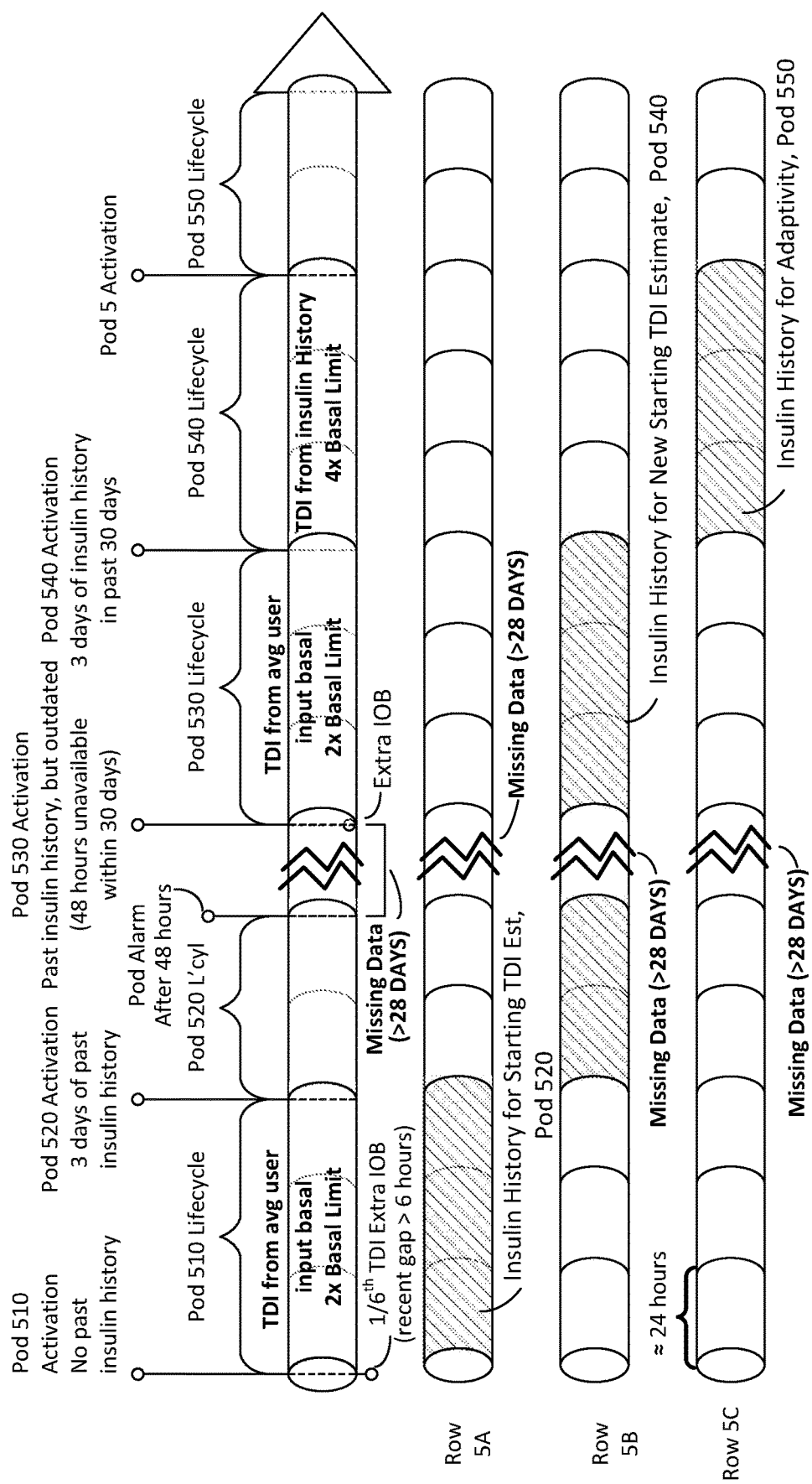
FIG. 5 shows a graphic illustrating, yet another example process related to an example situation related to use of a wearable drug delivery device.

Another example in which the process 100 of FIG. 1 reacts to an insufficient insulin delivery history is shown in FIG. 5. The example of FIG. 5 illustrates an example of the process 100 response to a long gap in insulin delivery history data. In the example of FIG. 5, during the activation of pod 510, the processor may be operable to note that there is insufficient insulin delivery history. As a result, in the example of FIG. 5, the processor may be operable to establish settings of the pod 510 for the insulin on board at $\frac{1}{6}^{th}$ of the total daily insulin. In addition, the safety boundary may be set at A times the basal insulin limit, or in this example, at 2 times the basal insulin limit.

As shown in row 5A, the pod 510 operates and provides data for its entire lifecycle. At the end of the lifecycle of pod 510, it is time to replace pod 510 with pod 520. At the activation of pod 520, the processor may be operable to determine that the insulin delivery history is sufficient and may set the safety boundary at B times the basal insulin limit and may set the total daily insulin, for example, as a weighted sum of a previous total daily insulin setting, and a daily average of insulin delivered according to a new insulin delivery history.

After a period of time, in this example, a continuous 48 hours, the pod 520 may cause the generation of an alarm indicating that the insulin delivery history is not being updated for some reason. In addition, no insulin delivery history is collected for over 28 days. For example, the user may discontinue use of a pod (e.g., a wearable drug delivery device) for some reason.

In this example, the missing data is greater than 28 days (e.g., 28 and a half or any fraction over 28 days). When the pod 530 is activated, the processor may be operable to determine the insulin delivery history is insufficient because, even though the last data in the insulin delivery history was from a continuous 48 hour period, the gap in the data was greater than 28 days which makes the data at the beginning of the continuous 48 hour period older than the 30 day threshold. As a result of the data at the beginning of the continuous 48 hour period being older than 30 days, the insulin delivery history is insufficient. Therefore, when the processor may be operable to use an average user input basal insulin value to set the total daily insulin, the safety boundary at 2 times the basal insulin limit and the gap flag to TRUE.

As shown in row 5B, the insulin delivery history from pod 530 is sufficient for the activation of pod 540. At the activation of pod 540, the processor may be operable to determine that the insulin delivery history is sufficient because the insulin delivery history was collected over a continuous 72 hours without a gap and the data in the 72 hours is not older than 30 days. Since the insulin delivery history is sufficient, the processor may be operable to set the safety boundary at B times (e.g., 4 or 6 times) the basal insulin limit and may set the total daily insulin, for example, as a daily average of insulin delivered according to a new insulin delivery history. Since pod 540 is the first pod with B times the basal insulin limit, the total daily insulin is set to the daily average of insulin delivered according to a new insulin delivery history. This may be considered a new starting TDI estimate for pod 540.

The sufficient insulin delivery history (as shown in row 5C) generated during the lifecycle of pod 540 enables the processor when activating pod 550 to use that sufficient insulin delivery history to generate a new total daily insulin value and maintain the safety boundary setting at B times (e.g., 4 times) the basal insulin limit. The pod 55 may begin operation in the adaptivity mode.

As discussed in the foregoing examples, every day the adaptivity and onboarding processes continually update the insulin history. For example, insulin delivery data collected each day may replace a previous history from the insulin delivery history as a result the AP algorithm more accurately estimates the insulin on board and adapts the total daily insulin to optimally match a user's insulin dosage requirements. So long as the user consistently uses the AP algorithm with the adaptivity mode enabled the automatic delivery of insulin automatically for approximately 7 days, approximately 80 percent of the difference between a current insulin value to a substantially optimal value is overcome.

In another example, the user may manually administer a dose of insulin prior to replacing a pod. As a result, the insulin on board may be greater than what is indicated by the insulin delivery history. The onboarding process may take this possibility into consideration and apply an insulin on board correction factor to allow a conservative delivery of insulin to avoid exceeding either the upper or lower safety boundary.

As discussed above, the disclosed processes and applications may include an adaptivity mode that modifies settings as the processor receives data from other components, such as a blood glucose sensor or wearable drug delivery device (i.e., a pod) that are explained in more detail with reference to FIG. 7.

Figure 6:
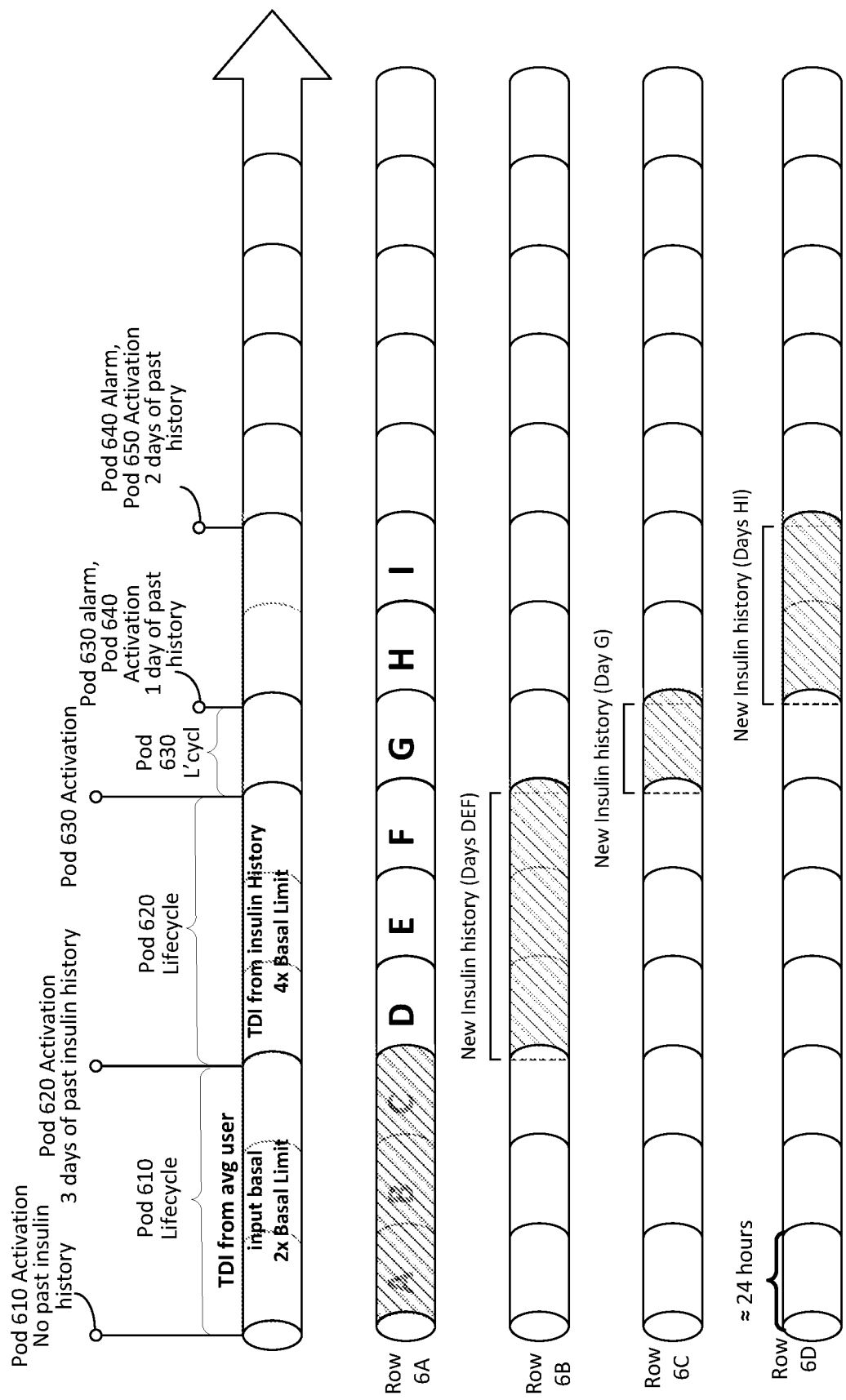
FIG. 6 shows a graphic illustrating an example process related to an added example situation related to use of a wearable drug delivery device.

The following is a discussion with reference to FIG. 6 of an example of an adaptivity process that is triggered when there is sufficient insulin delivery history to calculate an accurate estimate of the TDI. In the proposed example, if there is sufficient history based on the above assessments, the system can trigger the smart adaptivity process to take advantage of the known insulin delivery history and allow a relaxation of pre-existing safety bounds given the higher confidence of the user's insulin needs.

Goals of the adaptivity process are to: adjust onboarding TDI that may be different from a true TDI; compensate, in a short period of use since onboarding, for a significant portion of difference between onboarding TDI and true TDI (i.e., the actual user's TDI); and adjust TDI based on changing user needs (e.g., a teenage user getting older) that cannot be handled by an artificial pancreas algorithm.

It is anticipated that, over successive years of use, the adaptivity mode will improve the compensation for long term changes over time (such as a 26%+ increase/year; and 5-10× change over childhood years).

An example of the adaptivity mode is shown in the example of FIG. 6. As an initial activation of pod 610, no past insulin history is available, so the processor determines that the insulin delivery history is insufficient. Based on the determination of an insufficient insulin delivery history, the processor may set the total daily insulin level based on an average of a user input basal insulin dosage and the safety boundary at A (in the FIG. 6 example, A is equal to 2) times the basal limit. At the activation of the pod 610, the processor may, for example, generate a time stamp indicating a start of the lifecycle of the pod 610. In an example, the processor may generate a time stamp whenever a signal indicating the actuation of delivery insulin by the wearable drug delivery device or whenever an acknowledgment signal is received from a pod, such as pod 610.

Row 6A shows each day labeled A-I for which a pod (i.e., wearable drug delivery device) is in use. The processor may be operable when in adaptivity mode to collect insulin delivery data and blood glucose measurement data from a blood glucose sensor (described in more detail with reference to the example of FIG. 7), if available, for each of the respective days A-I. Of course, the processor may be operable to collect other data such as user input data related to meal carbohydrates, exercise, bolus dosages, insulin type, or the like.

In the example, during the lifecycle of pod 610, the processor may be operable to collect the insulin delivery history data for each of days A, B and C. At the end of the lifecycle of pod 610, the processor may be operable to activate pod 620. In an example, the processor may access the 3 days (i.e., days A, B and C) of insulin delivery history data during the activation of pod 620. Alternatively, the processor may obtain updated insulin delivery history data collected during operation of the wearable drug delivery device 610, which is the wearable drug delivery device being replaced. At the activation of pod 620, the processor using the insulin delivery history data collected during days A, B and C may determine that the insulin delivery history is sufficient and set the total daily insulin based on the insulin delivery history from days A, B and C. Alternatively, the processor may retrieve new information related to an amount of insulin delivered by the drug delivery device from an updated insulin delivery history. The processor may determine that adaptivity mode is active and in response may set a total daily insulin dosage at a weighted sum of a previously-set total daily insulin dosage and a daily average of insulin doses based on the updated insulin delivery history.

For example, the processor, when in adaptivity mode, may set the total daily insulin for pod 620 equal to the average insulin delivered over the past 3 days (e.g., A, B and C) according to Equation 2.

Eq. 2 $TDI_{pod620}=(I_A+I_B+I_C)/3$, where TDI is total daily insulin of a respective pod, $I_A$ is the insulin delivered for day A, $I_B$ is the insulin delivered for day B, and $I_C$ is the insulin delivered for day C.

The processor may set the TDI as shown in Equation 2 and may transmit the set total daily insulin dosage for receipt by a wearable drug delivery device (i.e., pod 620). The lifecycle of pod 620 may extend over days D, E and F. During the lifecycle of pod 620, the insulin delivery history may include data collected during days D, E and F as shown in Row 6B. The processor may remain in adaptivity mode as long as the insulin delivery history remains sufficient. At the activation of pod 630, the processor may set the total daily insulin for pod 630 based on a weighted sum of the previous total daily insulin setting (i.e., $TDI_{pod620}$) and an average of the average insulin delivered over the most recent 3 days (e.g., D, E and F). This is shown for example, in step 140 of FIG. 1. Equation 3 shows an example:

Eq. 3 $TDI_{pod630}=0.4*TDI_{pod620}+0.6*(I_D+I_E+I_F)/3$, where TDI is total daily insulin for a respective pod, $I_D$ is the insulin delivered for day D, $I_E$ is the insulin delivered for day E, $I_F$ is the insulin delivered for day F, and the divisor 3 is the number of days.

The weights 0.4 and 0.6, respectively, may be selected based on a confidence level of how reliable the insulin on board calculations are for a user over the lifecycle of a previous pod. For example, a weighted confidence may be generated based on a proportion of automatically delivered insulin doses to the number of user-input insulin doses delivered. In the example, the processor may maintain a count of a number of insulin doses automatically delivered by the wearable drug delivery device and a count of a number of user-input insulin doses delivered by the wearable drug delivery device over a time period. The time period may be, for example, a lifecycle of the previous pod or a day in a current lifecycle of the presently-implemented pod. The confidence may be weighted higher for the insulin deliveries during days with higher proportion of automated delivery as compared to user requested insulin deliveries. As a result of the higher confidence value, the most-recently determined total daily insulin value may be weighted greater. Alternatively, a low confidence score may cause the adaptivity algorithm to weight the most-recently determined total daily insulin value to be weighted less.

In some examples, a pod or wearable drug delivery device may malfunction but be replaced almost immediately with a new pod or wearable drug delivery device. Such a scenario is shown with respect to pod 630. As shown in Row 6C, data for the new insulin delivery history is collected only for 1 day, day G. A malfunction of pod 630 may cause an alarm to be generated. In response to the generated alarm, pod 630 may almost immediately be replaced with pod 640. As a result of the immediate replacement, no future data is shown as being missed from being collected, and there is no detectable gap in the new or updated insulin delivery history. At the activation of pod 640, the data collected for the new or updated insulin delivery history during lifecycle of pod 630 (i.e., day G) is used in determining a new total daily insulin estimate for pod 640. However, because a limited amount of data, in this example, the only one day of data, is added to the new or updated insulin delivery, the processor may adjust the weightings of the respective parameters as shown in Equation 4:

Eq. 4 $TDI_{pod640}=0.8*TDI_{pod630}+0.2\ I_G$, where TDI is total daily insulin for the respective pod and $I_G$ equals the average of the insulin delivered for day G.

The weights 0.8 and 0.2, respectively, may be selected based on a determination by the processor that the respective new insulin delivery history is limited to 1 day or less. Alternatively, or in addition, the weights 0.8 and 0.2 may be selected based on a weighted confidence as discussed above. Since the new insulin delivery history is limited, the new insulin delivery history may not be considered as reliable as the insulin delivery history used to determine the total daily insulin for pod 630 (i.e., $TDI_{pod630}$). As result, the processor may be operable to apply less weight (e.g., 0.2) to the average insulin delivered for day G and apply more weight (e.g., 0.8) to the previous pods total daily insulin setting (e.g., $TDI_{pod630}$).

As shown in Row 6D, pod 640 may operate for 2 days, days H and I before experiencing a malfunction. Pod 640 may generate an alarm in response to the malfunction. In response to the malfunction, pod 640 may almost immediately be replaced with pod 650. As a result of the immediate replacement, no future data is shown as being missed from being collected, and there is no detectable gap in the new or updated insulin delivery history. At the activation of pod 640, the processor may be operable to determine that the data collected for the new or updated insulin delivery history during lifecycle of pod 640 (i.e., days H and I) may be used to determine a new total daily insulin estimate for pod 650. In addition, the processor may be operable to determine that the new or updated insulin delivery history collected during the lifecycle of pod 640 includes two day of insulin delivery history as compared to the one day of insulin delivery history collected during the lifecycle of pod 630. As a result of the determination, the processor may be operable to adjust the weightings in the total daily insulin estimate for pod 650 (i.e., $TDI_{pod650}$). For example, the processor may set the total daily insulin as shown in Equation 5 below.

Eq. 5 $TDI_{pod650}=0.6*TDI_{pod640}+0.4*(I_H+I_I)/2$, where TDI is total daily insulin for the respective pod, $I_H$ is the insulin delivered for day H, and $I_I$ is the insulin delivered for day I.

As shown, the total daily insulin setting for each pod may be determined at the activation of the respective pod based on data collected during the lifecycle of a previous pod. In some examples, the insulin delivery history of the immediately previous pod may be considered most relevant for setting the total daily insulin.

In one example, the onboarding and adaptivity algorithm executed by the processor may maintain a count of a number of insulin doses automatically delivered by the wearable drug delivery device and a count of a number of user-input insulin doses delivered by the wearable drug delivery device over a time period, such as a day or 24 hours. As a result, instead of executing a generic sum of all insulin deliveries throughout the day, the processor may generate a "weighted confidence" of each day's total insulin delivery. For instance, if the onboarding and adaptivity algorithm is paired with a closed loop automatic insulin delivery algorithm (such as an artificial pancreas (AP) algorithm), there may be higher confidence of insulin deliveries matching a user's actual needs if there is a higher proportion of automated insulin deliveries (i.e., deliveries initiated by the AP algorithm) as compared to manual deliveries (i.e., deliveries initiated by a user). In this example, the adaptivity algorithm may assign a higher weight on the insulin deliveries during days with higher proportion of automated delivery as compared to user requested insulin deliveries.

A benefit of the adaptivity process as discussed above is the process's resiliency to short-term but large changes in insulin delivery while fulfilling the above referenced objectives of the adaptivity process. The adaptivity process executed while the processor is in adaptivity mode enables a robust implementation in response to missing data points. For example, sickness, missed boluses, or life events should not significantly impact long term changes in TDI estimates or insulin delivery. In addition, missing insulin history should not significantly impact TDI estimates.

Given these objectives, the proposed adaptivity approach seeks to assess all past insulin delivery history at each pod replacement cycle and execute an exponential moving average of daily insulin needs between the previous total insulin delivery values and the current insulin delivery value.

In the example, the overall adaptivity of insulin delivery histories, such as those described with reference to the examples of FIGS. 2-6, may be captured by the following equation 6:

Eq. 6  $TDI_N = (1 - F_{adapt} \cdot n_{days, new\ insulin\ data}) TDI_{N-1} + F_{adapt} \cdot \Sigma \text{new insulin data}$ Here, $TDI_N$ represents the estimate of the user's TDI for the $N^{th}$ adaptation step (or cycles of steps 105-170 of FIG. 1), and $F_{adapt}$ represents a convergence factor representing how fast the TDI estimate adapts to insulin delivery data from new insulin delivery histories. New insulin data represents any insulin delivery history that is available since last TDI calculation and was not utilized for the $(N-1)^{th}$ estimate of the user's TDI and $n_{days, new\ insulin\ data}$ represents the number of days for new insulin data that are available in the new insulin delivery history and the summation of the new insulin data of several days. For example, an Nth adaptation of a user's TDI may equal $TDI_N = (1 - 0.2 \cdot 3) TDI_{N-1} + 0.2 \cdot 3 \cdot (A+B+C)/3 = (1 - 0.2 \cdot 3) TDI + 0.2 \cdot (A+B+C)$, where $F_{adapt}$ is (0.2), 3 equals the $n_{days, new\ insulin\ data}$, $TDI_{N-1}$ is a previous TDI, and A, B and C represent a daily total insulin amount used by the user.

A variety of methods can be utilized to determine the optimal value of $F_{adapt}$. For example, several use cases can be reviewed to determine if the example value of this factor of 0.2 is relevant. This factor may be adjusted based on the rate of convergence to the user's actual TDI. The value of $F_{adapt}$ represents the rate at which the $N^{th}$ estimate of the TDI value converges to the user's actual TDI needs, with higher values of $F_{adapt}$ allowing more rapid convergence to the user's actual needs but increasing vulnerability to variations in the user's sensitivity. An optimal value of $F_{adapt}$ can be estimated by assessing average variations in user's insulin needs, and assessing the tolerable risk for over- or under-estimation of the user's TDI needs in case of noise. The optimal value of $F_{adapt}$ can then be the value that minimizes the risk while maximizing the rate of convergence to the user's actual average TDI needs (i.e., the average TDI needed to be delivered to this particular user).

The following figures show various use cases with different starting TDIs versus the true TDI of 48U, and the impact of varying daily insulin requirements and the system's sensitivity to these variations. The foregoing discussion of an onboarding algorithm and an adaptivity algorithm may be extended to incorporate other elements.

The process in the example of FIG. 1 and the examples of FIGS. 2-6 may be performed by a computer application executing on a personal diabetes management device (PDM), a smart phone, a wearable smart device (e.g., a smart watch, GPS device or the like), a long-term (e.g., one or two years of use) wearable insulin delivery device, or the like since the processing described above includes storing data, which may not be present on a pod or a wearable drug delivery device. However, a larger pump may have sufficient computing power and data storage capabilities to implement the described processes. These and other examples may be discussed in more detail with reference to the functional block diagram of an example of a diabetes treatment system shown in FIG. 7.

While a couple of hardware configuration examples were provided above, an alternative hardware configuration may make processing capabilities available on a pod or a wearable drug delivery device and, via wireless communication capabilities, any new data collected or previously collected data may be stored on another device within wireless communication range or accessible, via the other device within wireless communication range. For example, a pod may include a processor executing the computer application that enables the foregoing examples and that is operable to communicate with a smart phone. The smart phone may either store the new data collected or previously collected data or may be able to access a remote server, such as a cloud based server.

It may be helpful to discuss an example of a drug delivery system that may implement the process example of FIGS. 1-6. FIG. 7 illustrates an example of a drug delivery system 700.

The drug delivery system 700 may be operable to implement an AP application that includes functionality to provide an onboarding process and implement an adaptivity process to modify settings established during the onboarding process. The drug delivery system 700 may be an automated drug delivery system that may include a wearable drug delivery device (pump) 702, a blood glucose sensor 704, and a management device (PDM) 706. The system 700, in an example, may also include a smart accessory device 707, which may communicate with the other components of system 700 either via a wired or wireless communication link, such as 791-793.

In an example, the wearable drug delivery device 702 may be attached to the body of a user, such as a patient or diabetic, and may deliver any therapeutic agent, including any drug or medicine, such as insulin or the like, to a user.

The wearable drug delivery device 702 may, for example, be a wearable device worn by the user. For example, the wearable drug delivery device 702 may be directly coupled to a user (e.g., directly attached to a body part and/or skin of the user via an adhesive or the like). In an example, a surface of the wearable drug delivery device 702 may include an adhesive to facilitate attachment to a user.

The wearable drug delivery device 702 may include a number of components to facilitate automated delivery of a drug (also referred to as a therapeutic agent) to the user. The wearable drug delivery device 702 may be operable to store the drug and to provide the drug to the user. The wearable drug delivery device 702 is often referred to as a pump, or an insulin pump, in reference to the operation of expelling a drug from the reservoir 725 for delivery to the user. While the examples refer to the reservoir 725 storing insulin, the reservoir 725 may be operable to store other drugs or therapeutic agents suitable for automated delivery, such as morphine or the like.

In various examples, the wearable drug delivery device 702 may be an automated, wearable drug delivery device. For example, the wearable drug delivery device 702 may include a reservoir 725 for storing the drug (such as insulin), a needle or cannula (not shown) for delivering the drug into the body of the user (which may be subcutaneously), and a pump mechanism (mech.) 724, or other drive mechanism, for transferring the drug from the reservoir 725, through a needle or cannula (not shown), and into the user. The pump mechanism 724 may be fluidly coupled to reservoir 725, and communicatively coupled to the processor 721. The wearable drug delivery device 702 may also include a power source 728, such as a battery, a piezoelectric device, or the like, for supplying electrical power to the pump mechanism 724 and/or other components (such as the processor 721, memory 723, and the communication device 726) of the wearable drug delivery device 702. Although not shown, an electrical power supply for supplying electrical power may similarly be included in each of the sensor 704, the smart accessory device 707 and the personal diabetes management device (PDM) 706.

The blood glucose sensor 704 may be a device communicatively coupled to the processor 761 or 721 and may be operable to measure a blood glucose value at a predetermined time interval, such as every 5 minutes, or the like. The blood glucose sensor 704 may provide a number of blood glucose measurement values to the processor executing AP applications operating on the respective devices, such as 721, 761 and 771.

The wearable drug delivery device 702 may provide insulin stored in the reservoir 725 to the user based on information (e.g., blood glucose measurement values) provided by the sensor 704 and/or the personal diabetes management device (PDM) 706. For example, the wearable drug delivery device 702 may contain analog and/or digital circuitry that may be implemented as a processor 721 (or processor) for controlling the delivery of the drug or therapeutic agent. The circuitry used to implement the processor 721 may include discrete, specialized logic and/or components, an application-specific integrated circuit, a microcontroller device or processor that executes software instructions, firmware, programming instructions or programming code (enabling, for example, the artificial pancreas application (AP App) 729 as well as the process examples of FIGS. 1 and 3) stored in memory 723, or any combination thereof. For example, the processor 721 may execute a control algorithm, such as an artificial pancreas application 729, and other programming code that may make the processor 721 operable to cause the pump to deliver doses of the drug or therapeutic agent to a user at predetermined intervals or as needed based on the TDI settings discussed in the examples of FIGS. 1-6. The size and/or timing of the doses may be determined by, for example, an artificial pancreas application 729 or the like. In an example, the pump or wearable drug delivery device 702 is communicatively coupled to the processor 761 of the personal diabetes management device via the wireless link 720 or via a wireless link, such as 791 from smart accessory device 707 or 708 from the sensor 704. The pump mechanism 724 of the wearable drug delivery device may be operable to receive an actuation signal from the processor 761, and in response to receiving the actuation signal, expel insulin from the reservoir 725 according to the set insulin bolus dosage.

The other devices in the system 700, such as management device 706, smart accessory device 707 and sensor 704, may also be operable to perform various functions including controlling the wearable drug delivery device 702. For example, the personal diabetes management device 706 may include a communication device 764, a processor 761, and a management device memory 763. The personal diabetes management device memory 763 may store an instance of the AP application 769 that includes programming code, that when executed by the processor 761 provides the process examples described with reference to the examples of FIGS. 1-6. The personal diabetes management device memory 763 may also store programming code for providing the process examples described with reference to the examples of FIGS. 1-6.

The smart accessory device 707 may be, for example, an Apple Watch®, other wearable smart device, including eyeglasses, provided by other manufacturers, a global positioning system-enabled wearable, a wearable fitness device, smart clothing, or the like. Similar to the personal diabetes management device 706, the smart accessory device 707 may also be operable to perform various functions including controlling the wearable drug delivery device 702. For example, the smart accessory device 707 may include a communication device 774, a processor 771, a user interface 778, and a memory 773. The memory 773 may store an instance of the AP application 779 that includes programming code for providing the process examples described with reference to the examples of FIGS. 1-6. The memory 773 may also as store programming code and be operable to store data related to the AP application 779. The sensor 704 of system 700 may be a continuous glucose monitor (CGM) as described above, that may include a processor 741, a memory 743, a sensing or measuring device 744, and a communication device 746. The memory 743 may store an instance of an AP application 749 as well as other programming code and be operable to store data related to the AP application 749. The AP application 749 may also include programming code for providing the process examples described with reference to the examples of FIGS. 1-6. The user interface 778 may be presented on a touch-screen display device, a number of buttons and a presentation on a display, a combination of buttons and a touch-screen display presentation, or the like.

Instructions for determining the delivery of the drug or therapeutic agent (e.g., as a bolus dosage) to the user (e.g., the size and/or timing of any doses of the drug or therapeutic agent) may originate locally by the wearable drug delivery device 702 or may originate remotely and be provided to the wearable drug delivery device 702. In an example of a local determination of drug or therapeutic agent delivery, programming instructions, such as an instance of the artificial pancreas application 729, stored in the memory 723 that is coupled to the wearable drug delivery device 702 may be used to make determinations by the wearable drug delivery device 702. In addition, the wearable drug delivery device 702 may be operable to communicate with the cloud-based services 711 via the communication device 726 and the communication link 788.

Alternatively, the remote instructions may be provided to the wearable drug delivery device 702 over a wired or wireless link by the personal diabetes management device (PDM) 706, which has a processor 761 that executes an instance of the artificial pancreas application 769, or the smart accessory device 707, which has a processor 771 that executes an instance of the artificial pancreas application 769 as well as other programming code for controlling various devices, such as the wearable drug delivery device 702, smart accessory device 707 and/or sensor 704. The wearable drug delivery device 702 may execute any received instructions (originating internally or from the personal diabetes management device 706) for the delivery of the drug or therapeutic agent to the user. In this way, the delivery of the drug or therapeutic agent to a user may be automated.

In various examples, the wearable drug delivery device 702 may communicate via a wireless link 720 with the personal diabetes management device 706. The personal diabetes management device 706 may be an electronic device such as, for example, a smart phone, a tablet, a dedicated diabetes therapy management device, or the like. The personal diabetes management device 706 may be a wearable wireless accessory device. The wireless links 708, 720, 722, 791, 792 and 793 may be any type of wireless link provided by any known wireless standard. As an example, the wireless links 708, 720, 722, 791, 792 and 793 may enable communications between the wearable drug delivery device 702, the personal diabetes management device 706 and sensor 704 based on, for example, Bluetooth®, Wi-Fi®, a near-field communication standard, a cellular standard, or any other wireless optical or radio-frequency protocol.

The sensor 704 may be a glucose sensor operable to measure blood glucose and output a blood glucose value or data that is representative of a blood glucose value. For example, the sensor 704 may be a glucose monitor or a continuous glucose monitor (CGM). The sensor 704 may include a processor 741, a memory 743, a sensing/measuring device 744, and communication device 746. The communication device 746 of sensor 704 may include one or more sensing elements, an electronic transmitter, receiver, and/or transceiver for communicating with the personal diabetes management device 706 over a wireless link 722 or with wearable drug delivery device 702 over the link 708. The sensing/measuring device 744 may include one or more sensing elements, such as a glucose measurement, heart rate monitor, or the like. The processor 741 may include discrete, specialized logic and/or components, an application-specific integrated circuit, a microcontroller device or processor that executes software instructions, firmware, programming instructions stored in memory (such as memory 743), or any combination thereof. For example, the memory 743 may store an instance of an AP application 749 that is executable by the processor 741.

Although the sensor 704 is depicted as separate from the wearable drug delivery device 702, in various examples, the sensor 704 and wearable drug delivery device 702 may be incorporated into the same unit. That is, in various examples, the sensor 704 may be a part of the wearable drug delivery device 702 and contained within the same housing of the wearable drug delivery device 702 (e.g., the sensor 704 may be positioned within or embedded within the wearable drug delivery device 702). Glucose monitoring data (e.g., measured blood glucose values) obtained by the sensor 704 may be provided to the wearable drug delivery device 702, smart accessory device 707 and/or the personal diabetes management device 706 and may be used to determine total daily insulin settings, safety boundary settings, storage of data related to insulin delivery history or the like to enable improved automated delivery of insulin by the wearable drug delivery device 702.

The sensor 704 may also be coupled to the user by, for example, adhesive or the like and may provide information or data on one or more medical conditions and/or physical attributes of the user. The information or data provided by the sensor 704 may be used to adjust drug delivery operations of the wearable drug delivery device 702.

In an example, the personal diabetes management device 706 may be a personal diabetes manager. The personal diabetes management device 706 may be used to program or adjust operation of the wearable drug delivery device 702 and/or the sensor 704. The personal diabetes management device 706 may be any portable electronic device including, for example, a dedicated processor, such as processor 761, a smartphone, or a tablet. In an example, the personal diabetes management device (PDM) 706 may include a processor 761, a management device memory 763, and a communication device 764. The personal diabetes management device 706 may contain analog and/or digital circuitry that may be implemented as a processor 761 (or processor) for executing processes to manage a user's blood glucose levels and for controlling the delivery of the drug or therapeutic agent to the user. The processor 761 may also be operable to execute programming code stored in the personal diabetes management device management device memory 763. For example, the personal diabetes management device management device memory 763 may be operable to store an artificial pancreas application 769 that may be executed by the processor 761. The processor 761 may when executing the artificial pancreas application 769 may be operable to perform various functions, such as those described with respect to the examples in FIGS. 1 and 3. The communication device 764 may be a receiver, a transmitter, or a transceiver that operates according to one or more radio-frequency protocols. For example, the communication device 764 may include a cellular transceiver and a Bluetooth transceiver that enables the personal diabetes management device 706 to communicate with a data network via the cellular transceiver and with the sensor 704 and the wearable drug delivery device 702. The respective transceivers of communication device 764 may be operable to transmit signals containing information useable by or generated by the AP application or the like. The communication devices 726, 746 and 776 of respective wearable drug delivery device 702, sensor 704 and smart accessory device 707 may also be operable to transmit signals containing information useable by or generated by the AP application or the like.

The wearable drug delivery device 702 may communicate with the sensor 704 over a wireless link 708 and may communicate with the personal diabetes management device 706 over a wireless link 720. The sensor 704 and the personal diabetes management device 706 may communicate over a wireless link 722. The smart accessory device 707, when present, may communicate with the wearable drug delivery device 702, the sensor 704 and the personal diabetes management device 706 over wireless links 791, 792 and 793, respectively. The wireless links 708, 720, 722, 791, 792 and 793 may be any type of wireless link operating using known wireless standards or proprietary standards. As an example, the wireless links 708, 720, 722, 791, 792 and 793 may provide communication links based on Bluetooth®, Wi-Fi, a near-field communication standard, a cellular standard, or any other wireless protocol via the respective communication devices 726, 746 and 764. In some examples, the wearable drug delivery device 702 and/or the personal diabetes management device 706 may include a user interface 727 and 768, respectively, such as a keypad, a touchscreen display, levers, buttons, a microphone, a speaker, a display, or the like, that is operable to allow a user to enter information and allow the personal diabetes management device to output information for presentation to the user.

In various examples, the drug delivery system 700 may be an insulin drug delivery system. In various examples, the wearable drug delivery device 702 may be the OmniPod® (Insulet Corporation, Billerica, MA) drug delivery device as described in U.S. Pat. Nos. 7,303,549, 7,137,964, or 6,740,059, each of which is incorporated herein by reference in its entirety.

In various examples, the drug delivery system 700 may implement the artificial pancreas (AP) algorithm (and/or provide AP functionality) to govern or control automated delivery of insulin to a user (e.g., to maintain euglycemia—a normal level of glucose in the blood). The AP application may be implemented by the wearable drug delivery device 702 and/or the sensor 704. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 704). For example, the AP application may determine an appropriate delivery of insulin based on glucose level monitoring of the user through the sensor 704. The AP application may also allow the user to adjust insulin delivery. For example, the AP application may allow the user to issue (e.g., via an input) commands to the wearable drug delivery device 702, such as a command to deliver an insulin dosage or bolus dosage. In some examples, different functions of the AP application may be distributed among two or more of the personal diabetes management device 706, the wearable drug delivery device (pump) 702 or the sensor 704. In other examples, the different functions of the AP application may be performed by one device, such the personal diabetes management device 706, the wearable drug delivery device (pump) 702 or the sensor 704. In various examples, the drug delivery system 700 may operate according to or may include features or functionalities of the drug delivery systems described in U.S. patent application Ser. No. 15/359,187, filed Nov. 72, 7016, which is incorporated herein by reference in its entirety.

As described herein, the drug delivery system 700 or any component thereof, such as the wearable drug delivery device may be considered to provide AP functionality or to implement an AP application. Accordingly, references to the AP application (e.g., functionality, operations, or capabilities thereof) are made for convenience and may refer to and/or include operations and/or functionalities of the drug delivery system 700 or any constituent component thereof (e.g., the wearable drug delivery device 702 and/or the personal diabetes management device 706). The drug delivery system 700—for example, as an insulin delivery system implementing an AP application—may be considered to be a drug delivery system or an AP application-based delivery system that uses sensor inputs (e.g., data collected by the sensor 704).

In an example, one or more of the devices, 702, 704, 706 or 707 may be operable to communicate via a wireless communication link 788 with cloud-based services 711. The cloud-based services 711 may utilize servers and data storage (not shown). The communication link 788 may be a cellular link, a Wi-Fi link, a Bluetooth link, or a combination thereof, that is established between the respective devices 702, 706, or 707, and sensor 704 of system 700. The data storage provided by the cloud-based services 711 may store anonymized data, such as user weight, blood glucose measurements, age, meal carbohydrate information, or the like. In addition, the cloud-based services 711 may process the anonymized data from multiple users to provide generalized information related to the various parameters used by the AP application. For example, an age-based general target blood glucose value may be derived from the anonymized data, which may be helpful during an onboarding process when a wearable drug delivery device is activated as described. The cloud-based services 711 may also provide processing services for the system 700, such as performing the process 100 in the example of FIG. 2 or additional processes, such as that described below with reference to FIG. 3.

In an example, the wearable drug delivery device 702 may include a communication device 764, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 711. For example, outputs from the sensor 704 or the wearable drug delivery device (pump) 702 may be transmitted to the cloud-based services 711 for storage or processing via the transceivers of communication device 764. Similarly, wearable drug delivery device 702, management device 706 and sensor 704 may be operable to communicate with the cloud-based services 711 via the communication link 788.

In an example, the respective receiver or transceiver of each respective device, 702, 706 or 707, may be operable to receive signals containing respective blood glucose measurement values of blood glucose measurement values that may be transmitted by the sensor 704. The respective processor of each respective device 702, 706 or 707 may be operable to store each of the respective blood glucose measurement values in a respective memory, such as 723, 763 or 773. In addition, the respective memories 723, 763 or 773 may be operable to store information related to insulin delivery including an insulin delivery history as well as updates, including new data, to the insulin delivery history. The respective blood glucose measurement values may be stored as data related to the artificial pancreas algorithm, such as 729, 749, 769 or 779. In a further example, the AP application operating on any of the personal diabetes management device 706, the smart accessory device 707, or sensor 704 may be operable to transmit, via a transceiver implemented by a respective communication device, 764, 774, 746, a control signal for receipt by a wearable drug delivery device. In the example, the control signal may indicate an amount of insulin to be expelled by the wearable drug delivery device 702.

Various operational scenarios and examples of processes performed by the system 700 are described herein. For example, the system 700 may be operable to implement the process example of FIGS. 1-6. As a note, while 3 days are discussed in the examples, if a new generation of the pod or wearable drug delivery device, such as 702, may be usable for more than 3 days, then the lifecycles discussed in the examples of FIGS. 2-6 may be executed for the duration of the lifecycles of the new generation of pods.

The techniques described herein for providing onboarding and adaptivity processes as described herein for a drug delivery system (e.g., the system 700 or any component thereof) may be implemented in hardware, software, or any combination thereof. For example, the system 700 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A non-transitory computer readable medium embodied with programming code as part of an artificial pancreas application executable by a processor, and the processor when executing the programming code optimizes an upper safety boundary setting by causing the processor to perform functions, including functions to:

retrieve a portion of an insulin delivery history of at least a first wearable drug delivery device;

determine whether the portion of the insulin delivery history meets sufficiency requirements of an adaptivity mode of a second wearable drug delivery device;

in response to a determination that the insulin delivery history meets the sufficiency requirements, set an adaptivity flag of the second wearable drug delivery device to a value, wherein the second wearable drug delivery device is configured to operate in the adaptivity mode based on the value, wherein in the adaptivity mode the second wearable drug delivery device is configured to:

select an upper safety boundary as a limit for an amount of insulin to be delivered for a period of time;
set an amount of insulin to be delivered that is below the upper safety boundary;
and initiate delivery of an amount of insulin according to the set amount of insulin.

2. The non-transitory computer readable medium of claim 1, further embodied with programming code as part of the artificial pancreas application executable by the processor, and the processor, when executing the programming code to determine whether the portion of the insulin delivery history meets the sufficiency requirements, is further operable to:
analyze the retrieved portion of the insulin delivery history for predetermined criteria;
confirm, based on a result of the analysis, that the insulin delivery history meets the sufficiency requirements that satisfies a total number of hours of data within a contiguous period of time falling within a previous number of days; and
generate a confirmation signal indicating confirmation that the insulin delivery history meets the sufficiency requirements.

3. The non-transitory computer readable medium of claim 1, further embodied with programming code as part of the artificial pancreas application executable by the processor, and the processor when executing the programming code is operable to perform further functions to:
retrieve new information related to an amount of insulin delivered by the drug delivery device from an updated insulin delivery history;
determine that an adaptivity mode is active;
in response to the determination that the adaptivity mode is active, set a total daily insulin dosage at a weighted sum of a previously-set total daily insulin dosage and a daily average of insulin doses based on the updated insulin delivery history; and
transmit the set total daily insulin dosage for receipt by a wearable drug delivery device.

4. The non-transitory computer readable medium of claim 3, further embodied with programming code as part of the artificial pancreas application executable by the processor, and the processor when executing the programming code is operable to perform further functions to:
determine whether an insulin delivery was made within a predetermined last insulin delivery time period; and
in response to a determination that the insulin delivery was made within the predetermined last insulin delivery time period, send the selected safety boundary setting to the drug delivery device.

5. The non-transitory computer readable medium of claim 3, further embodied with programming code as part of the artificial pancreas application executable by the processor, and the processor when executing the programming code is operable to perform further functions to:
determine whether the drug delivery device made an insulin delivery within a predetermined last insulin delivery time period; and
in response to a determination that the drug delivery device did not make an insulin delivery within the predetermined last insulin delivery time period, establish a starting insulin on board setting equal to a percentage of the set total daily insulin dosage.

6. The non-transitory computer readable medium of claim 1, further embodied with further programming code as part of the artificial pancreas application executable by the processor, and the processor when executing the further programming code is operable to perform further functions, including functions to:
retrieve new information related to an amount of insulin delivered by the drug delivery device as part of an updated insulin delivery history, wherein the updated insulin delivery history is a sufficient insulin delivery history;
determine that an adaptivity mode is inactive;
in response to determining the adaptivity mode is inactive, set a total daily insulin dosage at a daily average based on the retrieved new information;
set the adaptivity mode to active; and
provide the set total insulin dosage to the drug delivery device.

7. The non-transitory computer readable medium of claim 6, further embodied with programming code as part of the artificial pancreas application executable by the processor, and the processor when executing the programming code is operable to perform further functions to:
determine whether the drug delivery device made an insulin delivery within a predetermined last insulin delivery time period; and
in response to a determination that the drug delivery device made an insulin delivery within the predetermined last insulin delivery time period, send the selected safety boundary setting to the drug delivery device.

8. The non-transitory computer readable medium of claim 6, further embodied with programming code as part of the artificial pancreas application executable by the processor, and the processor when executing the programming code is operable to perform further functions to:
determine whether the drug delivery device made an insulin delivery within a predetermined last insulin delivery time period; and
in response to a determination that the drug delivery device did not make an insulin delivery within the predetermined last insulin delivery time period, establish a starting insulin on board setting equal to a percentage of the set total daily insulin dosage.

9. The non-transitory computer readable medium of claim 1, further embodied with programming code as part of the artificial pancreas application executable by the processor, and the processor when executing the programming code to determine whether the portion of the insulin delivery history meets sufficiency requirements, is operable to:
determine that the portion of the insulin delivery history fails to meet the sufficiency requirements;
in response to a determination that the insulin delivery history fails to meet the sufficiency requirements, select a lower safety boundary for an amount of insulin to be delivered for a period of time, wherein the selected lower safety boundary is lower than the selected upper safety boundary and greater than a minimum amount of insulin to be delivered by the drug delivery device; and
limits the amount of insulin delivered by the wearable drug delivery device to at or below the selected lower safety boundary.

10. The non-transitory computer readable medium of claim 9, further embodied with programming code e as part of the artificial pancreas application executable by the processor, and the processor when executing the programming code is further operable to:
set the lower safety boundary at an insulin level equal to a multiplier applied a basal insulin limit setting, wherein the period of time is a day.

11. The non-transitory computer readable medium of claim 9, further embodied with programming code as part of the artificial pancreas application executable by the processor, and the processor when executing the programming code is further operable to:

provide an indication that an adaptivity mode is inactive.

12. The non-transitory computer readable medium of claim 1, further embodied with programming code as part of the artificial pancreas application executable by the processor, and the processor, when determining whether the insulin delivery history is sufficient, is further operable to:

determine that data in the insulin delivery history:
spans a total of approximately 48 hours without a gap greater than approximately 6 hours over a contiguous period of time of approximately 54 hours; and
is not older than approximately 30 days.

13. The non-transitory computer readable medium of claim 1, further embodied with programming code as part of the artificial pancreas application executable by the processor, and the processor, when determining whether the insulin delivery history is sufficient, is further operable to:

retrieve new information relates to an amount of insulin delivered by the drug delivery device from an updated insulin delivery history and
determine that an adaptivity mode is active or inactive.

14. The non-transitory computer readable medium of claim 1, further embodied with programming code as part of the artificial pancreas application executable by the processor, and the processor, when determining whether the insulin delivery history is sufficient, is further operable to:

in response to a determination that an adaptivity mode is active, set a total daily insulin at a weighted sum of a previously-set total daily insulin dosage and a daily average of insulin doses based on an updated insulin delivery history; or
in response to the determination that the adaptivity mode is inactive, set or retain a total daily insulin based on a user input basal insulin dosage.

* * * * *